United States Patent
Le et al.

(10) Patent No.: US 6,224,570 B1
(45) Date of Patent: May 1, 2001

(54) RHEOLYTIC THROMBECTOMY CATHETER AND METHOD OF USING SAME

(75) Inventors: Hieu V. Le, Minneapolis; Michael J. Bonnette, Afton; John Edward Morris, Minneapolis; Steven E. Wiesel, Montrose; Debra M. Kozak, Centerville; Cindy M. Setum, Plymouth; Robert G. Dutcher, Maple Grove, all of MN (US)

(73) Assignee: Possis Medical, Inc., Minneapolis, MN (US)

( * ) Notice: Subject to any disclaimer, the term of this patent is extended or adjusted under 35 U.S.C. 154(b) by 0 days.

(21) Appl. No.: 09/188,633

(22) Filed: Nov. 9, 1998

Related U.S. Application Data

(63) Continuation-in-part of application No. 09/019,728, filed on Feb. 6, 1998, now Pat. No. 5,989,210.

(51) Int. Cl.$^7$ .................................................. A61M 5/178
(52) U.S. Cl. ................................ 604/165.02; 604/165.04
(58) Field of Search ............................... 604/19, 22, 35, 604/165.01, 500, 508–509, 510, 164.01, 164.03, 164.09, 164.1, 164.11, 164.13, 165.02, 165.04, 167.06, 170.01, 170.02, 264, 523–525, 529, 533–536, 177, 174, 165.03; 606/167.01

(56) References Cited

U.S. PATENT DOCUMENTS

| | | | |
|---|---|---|---|
| 4,224,943 | * | 9/1980 | Johnson et al. . |
| 4,248,234 | | 2/1981 | Assenza et al. . |
| 4,385,635 | | 5/1983 | Ruiz . |
| 4,781,186 | * | 11/1988 | Simpson et al. . |
| 4,790,813 | * | 12/1988 | Kensey ................................... 604/22 |
| 4,950,238 | * | 8/1990 | Sullivan .................................. 604/22 |
| 5,092,873 | * | 3/1992 | Simpson et al. ...................... 606/159 |
| 5,135,482 | * | 8/1992 | Neracher ................................ 604/22 |
| 5,215,614 | | 6/1993 | Wijkamp et al. . |
| 5,221,270 | | 6/1993 | Parker . |
| 5,234,416 | | 8/1993 | Macaulay et al. . |
| 5,250,059 | | 10/1993 | Andreas et al. . |
| 5,300,022 | * | 4/1994 | Klapper et al. ........................ 604/35 |
| 5,318,518 | * | 6/1994 | Plechinger et al. .................... 604/43 |
| 5,358,485 | * | 10/1994 | Vance et al. ........................... 604/22 |
| 5,370,609 | * | 12/1994 | Drasler et al. ......................... 604/22 |
| 5,380,307 | | 1/1995 | Chee et al. . |
| 5,928,186 | * | 7/1999 | Homsma et al. ....................... 604/22 |
| 5,997,558 | * | 12/1999 | Nash ...................................... 606/159 |

* cited by examiner

Primary Examiner—Richard K. Seidel
Assistant Examiner—LoAn H. Thanh
(74) Attorney, Agent, or Firm—Hugh D. Jaeger

(57) ABSTRACT

A rheolytic thrombectomy catheter and method of using same to remove thrombus from a body vessel or other body cavity. Several embodiments are disclosed. All embodiments include an outer catheter having a lumen and an inner high pressure tube of a size to enable it to be passed through the lumen of the catheter. The distal end of the inner high pressure tube extends beyond the distal end of the catheter and carries a jet cap for directing one or more jets of saline proximally toward the distal end of the catheter. In some embodiments, the catheter has a distally located inwardly directed stationary stop and the inner high pressure tube includes a distally located outwardly directed transitional stop for engaging the inwardly directed stationary stop to thereby position the jet cap at a defined distance from the distal end of the catheter. In other embodiments, a stationary stop is located at the proximal end of the catheter and a transitional stop is carried on the proximal end of the inner high pressure tube. In the embodiments having the stationary and transitional stops located proximally, the inner high pressure tube includes a flow director at its distal end. In use, thrombus is dislodged, entrained, and broken into pieces by the saline jets and evacuated proximally through the lumen of the catheter.

39 Claims, 36 Drawing Sheets

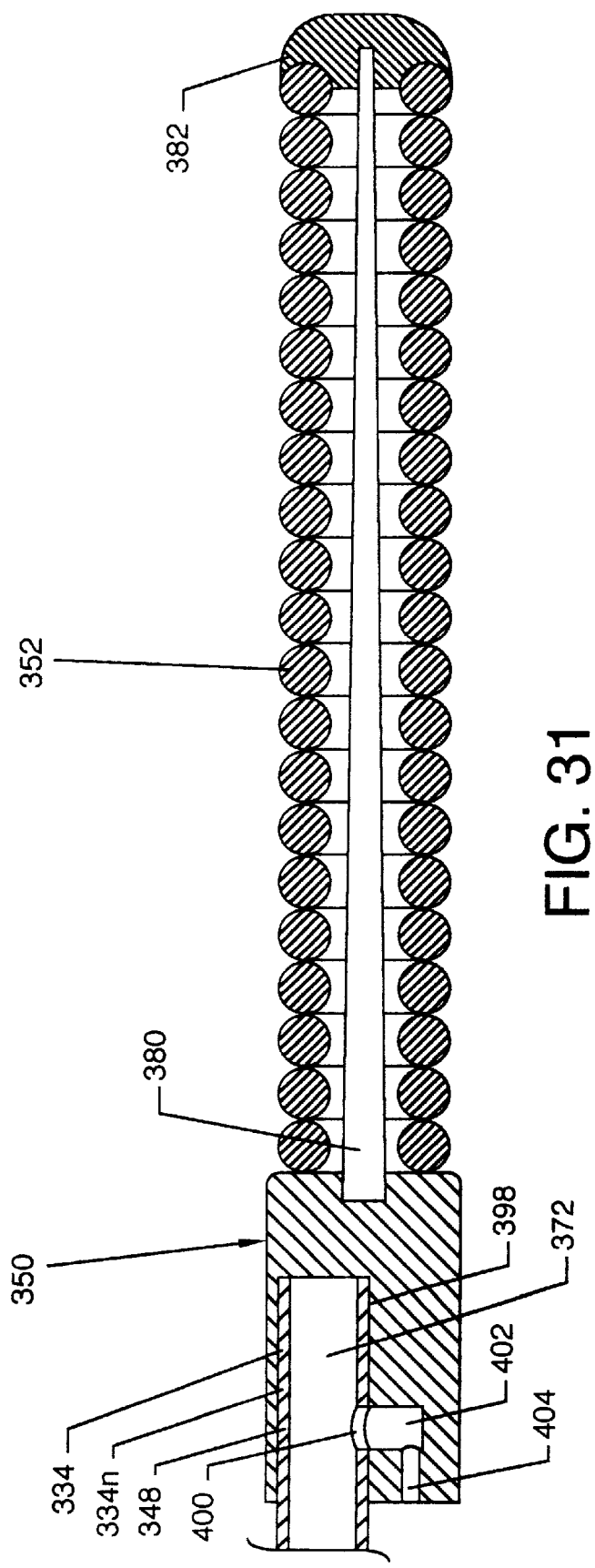

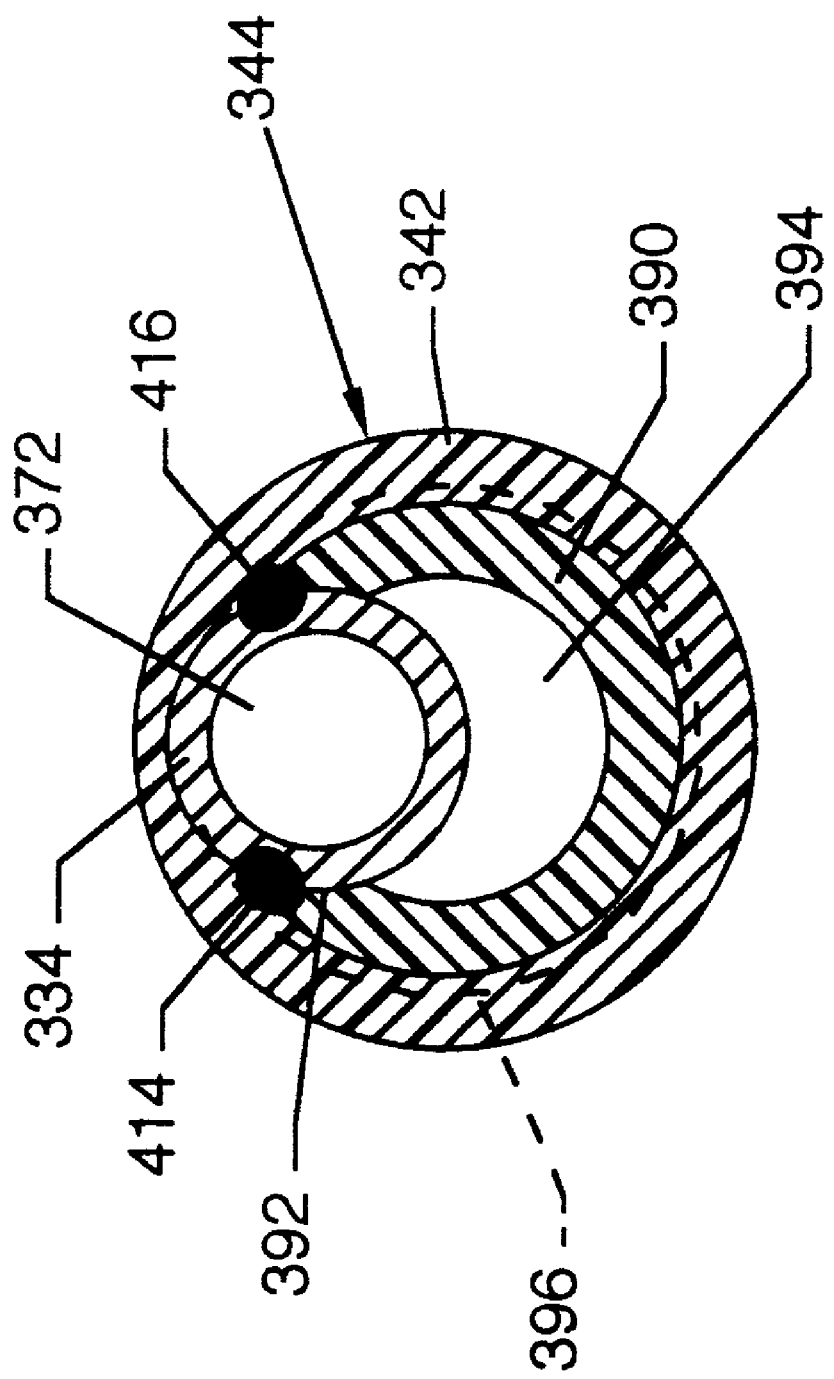

RHEOLYTIC THROMBECTOMY CATHETER AND METHOD OF USING SAME

CROSS REFERENCES TO CO-PENDING APPLICATIONS

This patent application is a continuation-in-part of Ser. No. 09/019,728 entitled "Rheolytic Thrombectomy Catheter and Method of Using Same" filed on Feb. 06, 1998, now U.S. Pat. No. 5,989,210 issued Nov. 23, 1999.

BACKGROUND OF THE INVENTION

1. Field of the Invention

The present invention relates to a rheolytic thrombectomy catheter and method of using same to remove thrombus from a body vessel or other body cavity.

2. Description of the Prior Art

Procedures and apparatus have been developed for ease in removing tissue and various deposits. Several such devices employ a jet of saline as the working tool to help break up the tissue deposit and further provide a suction means to remove the deposit. U.S. Pat. No. 5,135,482 to Neracher describes a hydrodynamic device for removal of organic deposit from a human vessel. A supply of saline is delivered by a high pressure duct to the distal end of a catheter. The saline exits the duct as a jet that is directed generally forward and directly toward the tissue to be broken up. The duct is contained within and can move axially with respect to a hose that is positioned around the duct. A vacuum suction is applied to the hose to remove the debris that is created from the broken-up tissue. This device is not intended to pass through tortuous pathways found in the fragile vessels of the brain, and any attempt to employ the device for such purpose would be far too traumatic to the patient.

Another drainage catheter, described by Griep in U.S. Pat. No. 5,320,599, has a discharge channel and a pressure channel. The channels are formed into a single catheter tube such that the two tubes are fixed with respect to each other. This catheter could not provide the flexibility needed to negotiate the tortuous vascular pathways found in the vessels of the brain.

SUMMARY OF THE INVENTION

The general purpose of the present invention is to provide a rheolytic thrombectomy catheter and method of using same to remove thrombus from a body vessel or other body cavity.

The present invention, a rheolytic thrombectomy catheter, is a surgical device for removal of material such as thrombus from a vessel or other body cavity. As shown in one or more embodiments, a rheolytic thrombectomy catheter for removing tissue from a vessel or other body cavity includes an outer assembly comprising a first tube or catheter having a lumen with an open distal end and an internally and distally located stationary stop partially obstructing the lumen at the open distal end, the lumen being of a diameter sufficient to allow passage of a guidewire; and an inner assembly comprising a high pressure second tube or hypo-tube having a high pressure lumen and a distal end having one or more orifices, a distally located transitional stop fixed to the high pressure hypo-tube adjacent to the distal end, and a jet cap positioned at the hypo-tube distal end for directing one or more jets of saline toward the distal end of the catheter, the inner assembly being movable axially within the outer assembly such that the distally located transitional stop engages the distally located stationary stop to hold the jet cap in a desired relationship with respect to the distal end of the catheter.

In another embodiment, a rheolytic thrombectomy catheter for removing thrombus or other body tissue from an obstructed body vessel or other body cavity includes an outer assembly including an evacuation tube having a proximal end and an open distal end containing a distally located stationary stop and having an evacuation lumen that is of a diameter sufficient to allow passage of a standard coronary or interventional neuroradiological guidewire; and an inner assembly including a high pressure hypo-tube having a high pressure lumen, the high pressure hypo-tube having a proximal end and a distal end, the distal end having one or more orifices through which saline can exit from the high pressure lumen to be directed toward the open distal end of the evacuation tube, a distally located transitional stop fixed to the high pressure hypo-tube at a position closer to the distal end than to the proximal end, and a jet cap positioned at the distal end of the high pressure hypo-tube, the jet cap coacting with the high pressure hypo-tube to direct one or more jets of saline toward the open distal end of the evacuation tube.

Preferably, the rheolytic thrombectomy catheter has a guidewire coil attached at the distal end of the jet cap to allow advancement of the inner assembly and the outer assembly together within the vasculature. Preferably, the rheolytic thrombectomy catheter has a jet cap which directs a jet of saline toward the distal end of the catheter, which functions as an evacuation tube. Preferably, the rheolytic thrombectomy catheter includes a high pressure hypo-tube with at least one orifice and a jet cap configured and arranged for directing one or more jets of saline to impinge upon or near the distal end of the catheter. The rheolytic thrombectomy catheter preferably is flexible and can pass over a standard guidewire through tortuous vascular pathways.

The present invention also provides a method of removing thrombus from an obstructed body vessel. The method includes the steps of:

a. providing a guidewire and an outer assembly including a catheter having a distal end and an internally located stationary stop positioned adjacent to the distal end;

b. advancing the guidewire to a vascular site containing thrombus;

c. advancing the catheter over the guidewire to the vascular site containing thrombus to position the distal end at the vascular site;

d. removing the guidewire from the catheter;

e. providing an inner assembly including a hypo-tube carrying a jet cap and a transitional stop spaced apart from the jet cap;

f. advancing the inner assembly within the catheter of the outer assembly to engage the transitional stop with the stationary stop; and, g. providing a high pressure saline supply to the hypo-tube so as to cause a jet of saline to emanate from the jet cap and to entrain thrombus into a gap or space where the thrombus is macerated and then pushed into the catheter for removal from the body; and, h. providing impingement of the jet on the evacuation lumen to create sufficient stagnation pressure to allow evacuation of debris with no need for additional suction on the proximal end of the evacuation lumen.

In the method, preferably, the jet cap carries a distally projecting guidewire coil to facilitate further distal advancement of the inner assembly and the outer assembly together within the vasculature to a further vascular site containing thrombus so as to remove additional distally situated thrombus.

The present invention is also a catheter combination including a first tube or catheter, being a part of an outer assembly, the first tube having a proximal end, an open distal end, and a lumen extending between the proximal end and the open distal end; a second tube or hypo-tube, being a part of an inner assembly, the second tube being separable from the first tube and being insertable within the lumen of the first tube, the second tube having a proximal end, a distal end, and a lumen extending between the proximal end and the distal end; a jet cap, being also a part of the inner assembly, the jet cap being connected to the second tube at the distal end of the second tube for directing fluid exiting the lumen of the second tube, the jet cap being capable of passage through the lumen of the first tube and being characterized by the ability to provide a localized region of low pressure associated with a liquid flow directed generally proximally and into the lumen of the first tube through the open distal end of the first tube when the jet cap is located and oriented appropriately relative to the open distal end of the first tube; and means for indexing an appropriate positional relationship of the jet cap and distal end of the second tube relative to the open distal end of the first tube. The means for indexing preferably includes a distally located stationary stop projecting inward from the first tube and a distally located transitional stop projecting outward from the second tube. When the second tube is advanced within the first tube, the stops mutually engage to control the orientation and spacing and relationship between the jet cap and the open distal end of the first tube. More preferably, the stops are each tapered to additionally laterally position the second tube within the first tube. Most preferably, the centering causes the tubes to become concentric. Preferably, one or both stops interact, when engaged, to preserve a channel for fluid flow rather than fully obstructing the cavity between the first tube and the second tube.

Another embodiment group provides a catheter combination including a first tube or catheter, being a part of an outer assembly, the first tube having a proximal end, a manifold attached thereto, an open distal end, and a lumen extending between the proximal end and the open distal end; a second tube or hypo-tube, being a part of an inner assembly, the second tube being separable from the first tube and being insertable within the lumen of the first tube, the second tube having a proximal end, a distal end, and a lumen extending between the proximal end and the distal end; a flow director including an inner body and an expandable exhaust tube each being located near but not at the second tube distal end, a pressure operated closeable or sealable annulus between the outer surface of the expandable exhaust tube and the catheter interior annular surface, a jet cap, being also a part of the inner assembly, the jet cap being connected to the second tube at the distal end of the second tube for directing fluid proximally for thrombus oblation and subsequently through a lumen in the flow director and the lumen of the first tube, the jet cap being capable of passage through the lumen of the first tube and being characterized by the ability to provide a localized region of low pressure associated with a liquid flow directed generally proximally and into the inner body, the expandable exhaust tube and lumen of the first tube and through the distal end of the first tube when the jet cap is located and oriented appropriately, as desired, relative to the inner body at the distal end of the first tube; and, a variable deployment distance means for indexing an appropriate positional and variable relationship of the jet cap and a tapered core tip at the distal end of the second tube relative to the distal end of the first tube. A stop means is provided for limiting movement of the jet cap and tapered core tip preferably including a proximally located hemostasis nut/stop at the proximal end of a manifold at the proximal end of the first tube, and a proximally located filter housing/high pressure connection stop assembly projecting outwardly and proximally from the proximal end of the second tube. When the second tube is advanced within the first tube, fluoro-imaging can be incorporated to provide adequate spacing and relationship between the jet cap or guidewire coil and the distal end of the first tube. This relationship is also referred to as variable deployment distance. Lateral positioning of the second tube within the first tube is readily accomplished during the first stage (insertion) in an unpressurized operational mode where the closeable annulus is suitably sized to allow easy unrestricted passage of the second tube within and through the first tube. During the operational pressurized mode, jetted saline causes the expandable exhaust tube to expand, thus closing and eliminating the open annulus to pressure seal the first tube to the second tube, but still allowing movement relative to each other.

The above alternative embodiment group embodiment of the present invention also provides a method of removing thrombus from an obstructed body vessel. The method includes the steps of:

a. providing a guidewire and an outer assembly including a catheter having an interior annular surface, a distal end, and an externally located stationary hemostasis nut/stop positioned adjacent to the proximal end;

b. advancing the guidewire to a vascular site containing thrombus;

c. advancing the catheter over the guidewire to the vascular site containing thrombus to position the distal end at the vascular site;

d. removing the guidewire from the catheter;

e. providing an inner assembly including a hypo-tube carrying a jet cap at its distal end, a flow director including an expandable exhaust tube proximal of the jet cap, and a transitional filter housing/high pressure connection/stop assembly at its proximal end;

f. advancing the inner assembly to a desired position within the catheter of the outer assembly, so that a gap proximal to the jet cap extends past the distal end of the catheter;

g. providing a high pressure saline supply to the hypo-tube so as to cause a jet of saline to emanate from the jet cap and to entrain thrombus into a gap or space where the thrombus is macerated and then pushed into the catheter for removal from the body; and, h. providing impingement of the jet on the evacuation lumen to create sufficient stagnation pressure to allow evacuation of debris with no need for additional suction on the proximal end of the evacuation lumen.

In the method, preferably, the jet cap carries a distally projecting guidewire coil to facilitate further distal advancement of the inner assembly and the outer assembly together or independently within the vasculature to a further vascular site containing thrombus so as to remove additional distally situated thrombus.

One significant aspect and feature of the present invention is the variously designed jet caps which are oriented to direct jets of saline in a proximal direction.

Another significant aspect and feature of the present invention is the stationary stop at the distal end of the catheter and the distally located transitional stop on the hypo-tube which together coact to position a jet cap at a defined distance beyond the distal end of the catheter.

Still another significant aspect and feature of the present invention is the distally located transitional stop which has an evacuation lumen and a hypo-tube receiving hole which is offset from the longitudinal axis of the distally located transitional stop.

Yet another significant aspect and feature of the present invention is the provision of complementary angled surfaces on the distally located stationary and transitional stops which upon engagement serve to center the inner assembly within the outer assembly.

A further significant aspect and feature of the present invention is the distally located stationary stop which is formed unitarily with the wall of the catheter at the distal end of the catheter.

A still further significant aspect and feature of the present invention is the guidewire coil provided at the distal end of the jet cap to allow advancement of the inner assembly and the outer assembly together or independently within the vasculature.

As found in additional embodiment groups there is also provided other significant aspects and features of the present invention including the use of a transitional filter housing/high pressure connection/stop assembly proximally located on the inner assembly and a stationary hemostasis nut/stop proximally located on the outer assembly to prevent the inner assembly from being excessively advanced, so that the expandable tube proximal end does not become disengaged from the distal end of the catheter.

A further significant aspect and feature as found in additional embodiment groups is an annulus which is open for lateral movement of the inner assembly within the outer assembly during the initial unpressurized mode (insertion) and which is closed and sealed by jetted saline during the oblation process to provide maximum proximally directed saline flow without leakage between the outer and inner assemblies when thrombotic tissue is broken up and carried proximally.

Having thus described embodiments and significant aspects and features of the present invention, it is the principal object of the present invention to provide a rheolytic thrombectomy catheter and method of using same to remove thrombus from a body vessel.

One object of the present invention is to provide a rheolytic thrombectomy catheter of such size, flexibility and construction as to enable it to pass readily through the tortuous pathways found in the fragile vessels of the brain.

Another object of the present invention is to provide a rheolytic thrombectomy catheter with means for producing one or more jets of saline and projecting them in a proximal direction toward a site of thrombus and toward an evacuation passage.

Yet another object of the present invention is to provide a rheolytic thrombectomy catheter with means for producing one or more jets of saline and with indexing means to position the jet producing means at a prescribed location at the distal end of the catheter.

Still another object of the present invention is to provide a rheolytic thrombectomy catheter of the type having an inner assembly that is insertable into an outer assembly with stop means for limiting the extent to which the inner assembly can be inserted into the outer assembly.

A further object of the present invention is to provide a rheolytic thrombectomy catheter of the type having an inner assembly and an outer assembly with means which centers the inner assembly within the outer assembly and which orients the parts of the inner assembly in a prescribed manner with respect to the parts of the outer assembly.

A still further object of the present invention is to provide an improved method of removing thrombus from an obstructed body vessel.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 31 is a view in cross section of the jet cap and the guidewire coil along line 31—31 of FIG. 27;

FIG. 32 is a view in cross section of the junction of the inner body and the expandable exhaust tube along line 32—32 of FIG. 30;

DETAILED DESCRIPTION OF THE PREFERRED EMBODIMENTS

Figure 1:
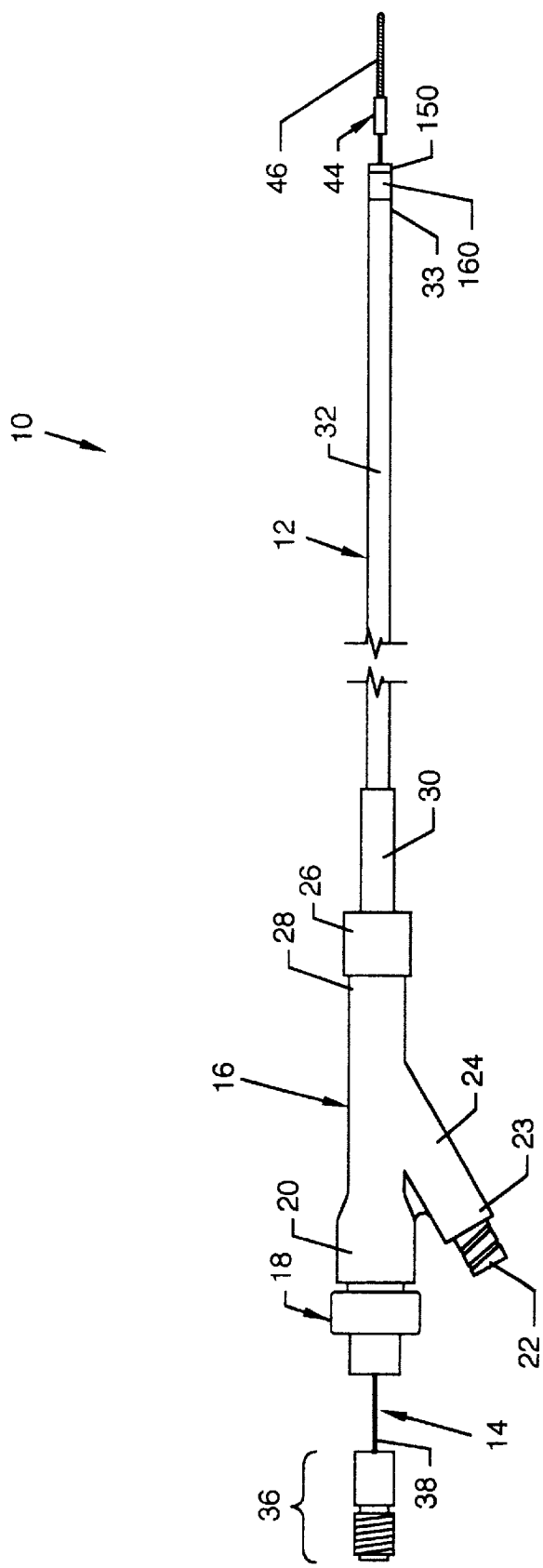
FIG. 1 is a side view of the present invention, a rheolytic thrombectomy catheter useful for the removal of thrombus.
Figure 2:
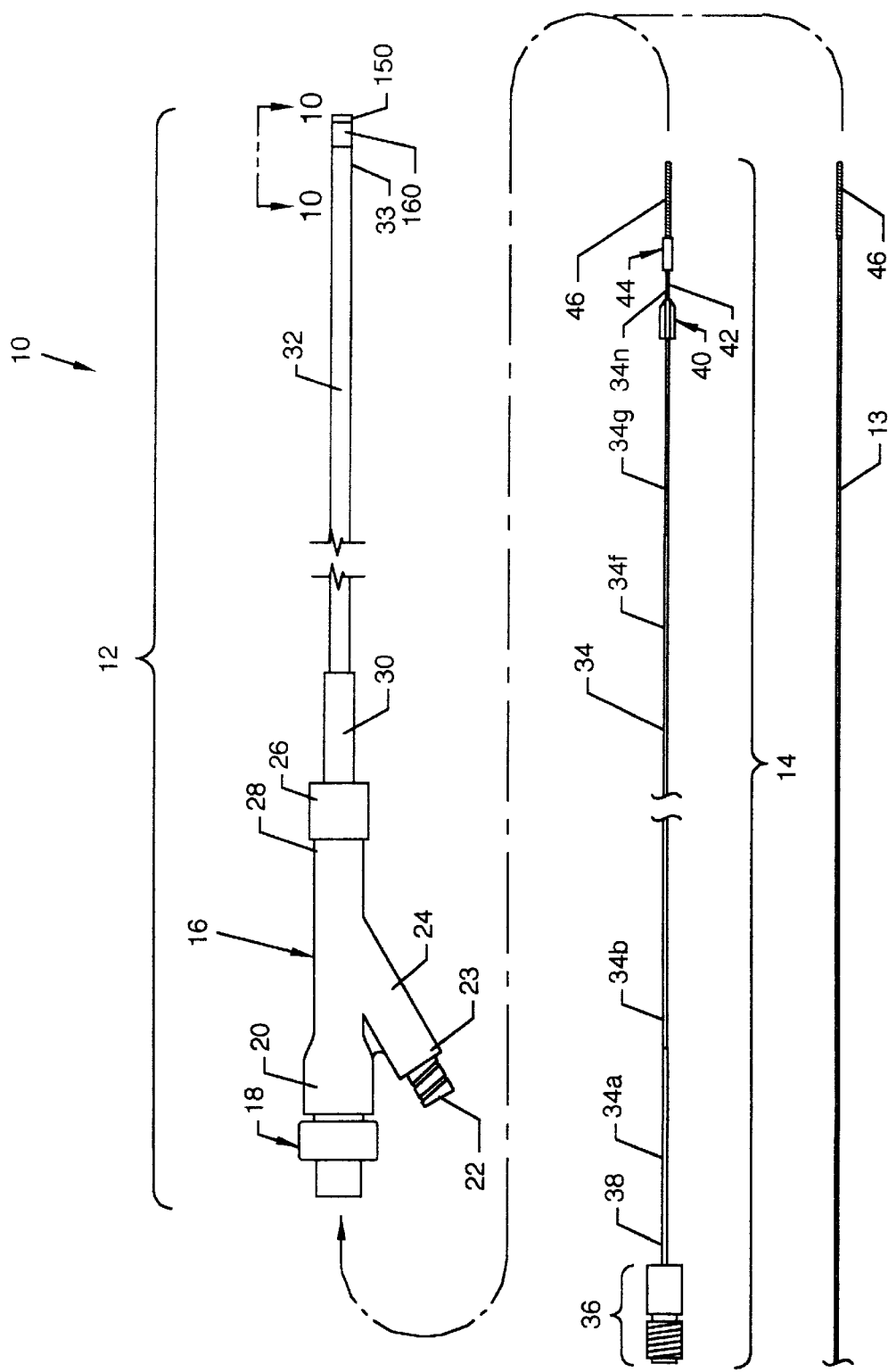
FIG. 2 is a semi-exploded side view of the rheolytic thrombectomy catheter depicting the two major assemblies thereof, viz., an outer assembly and an inner assembly.

FIG. 1 illustrates a side view of a rheolytic thrombectomy catheter 10 useful for the removal of thrombus, and FIG. 2 illustrates a semi-exploded side view of the rheolytic thrombectomy catheter 10. The rheolytic thrombectomy catheter 10 includes two major assemblies: namely, an outer assembly 12 and an inner assembly 14. The inner assembly 14 aligns concentrically to and within the outer assembly 12 and extends beyond the length of the outer assembly 12. Externally visible components, or portions of components, of the outer assembly 12 of the rheolytic thrombectomy catheter 10, as illustrated in FIGS. 1 and 2, include a manifold 16, also known as a Y-adapter, a hemostasis nut 18 secured in the proximal end 20 of the manifold 16, a Luer connection 22 located at the proximal end 23 of an angled manifold branch 24 extending from the manifold 16, a Luer fitting 26 secured to the distal end 28 of the manifold 16, a strain relief 30 secured to the distal end 28 of the manifold 16 by the Luer fitting 26, and a first tube or catheter 32, having a distal end 33, secured to the manifold 16 by the strain relief 30 and Luer fitting 26. The externally visible components of the inner assembly 14, illustrated in FIG. 2, include a high pressure second tube or hypo-tube 34, a filter housing/high pressure connection assembly 36 concentrically aligned to and secured over and about the hypo-tube proximal end 38, a configured transitional stop 40 concentrically aligned to and secured over and about the hypo-tube 34 at a point near and adjacent to the hypo-tube distal end 42, a jet cap 44 concentrically aligned to and secured over and about the hypo-tube 34 at the hypo-tube distal end 42, and a guidewire coil 46 concentrically aligned to and secured to one end of the jet cap 44. The high pressure hypo-tube 34 is drawn and is tapered in incremental steps to provide degrees of flexibility along its length. For purposes of example and illustration, the hypo-tube 34 can include a hypo-tube portion 34a at the hypo-tube proximal end 38 having an outer diameter of 0.018 inch or smaller, and can include a plurality of incrementally stepped down hypo-tube portions 34b–34n each of lesser outer diameter, where the last hypo-tube portion 34n is stepped down to an outer diameter of 0.008 inch at the hypo-tube distal end 42. The hypo-tube 34 becomes increasingly more flexible from the hypo-tube proximal end 38 towards the hypo-tube distal end 42 due to the incremental diameter decrease along its length. Increasing flexibility along the length of the hypo-tube 34 allows for easier flexed penetration into tortuous vascular paths. Although the hypo-tube 34 is stepped down in increments, the hypo-tube 34 can also be fashioned of a constantly decreasing outer diameter to provide increasing flexibility along its length and shall not be construed to be limiting to the scope of the invention.

Figure 3:
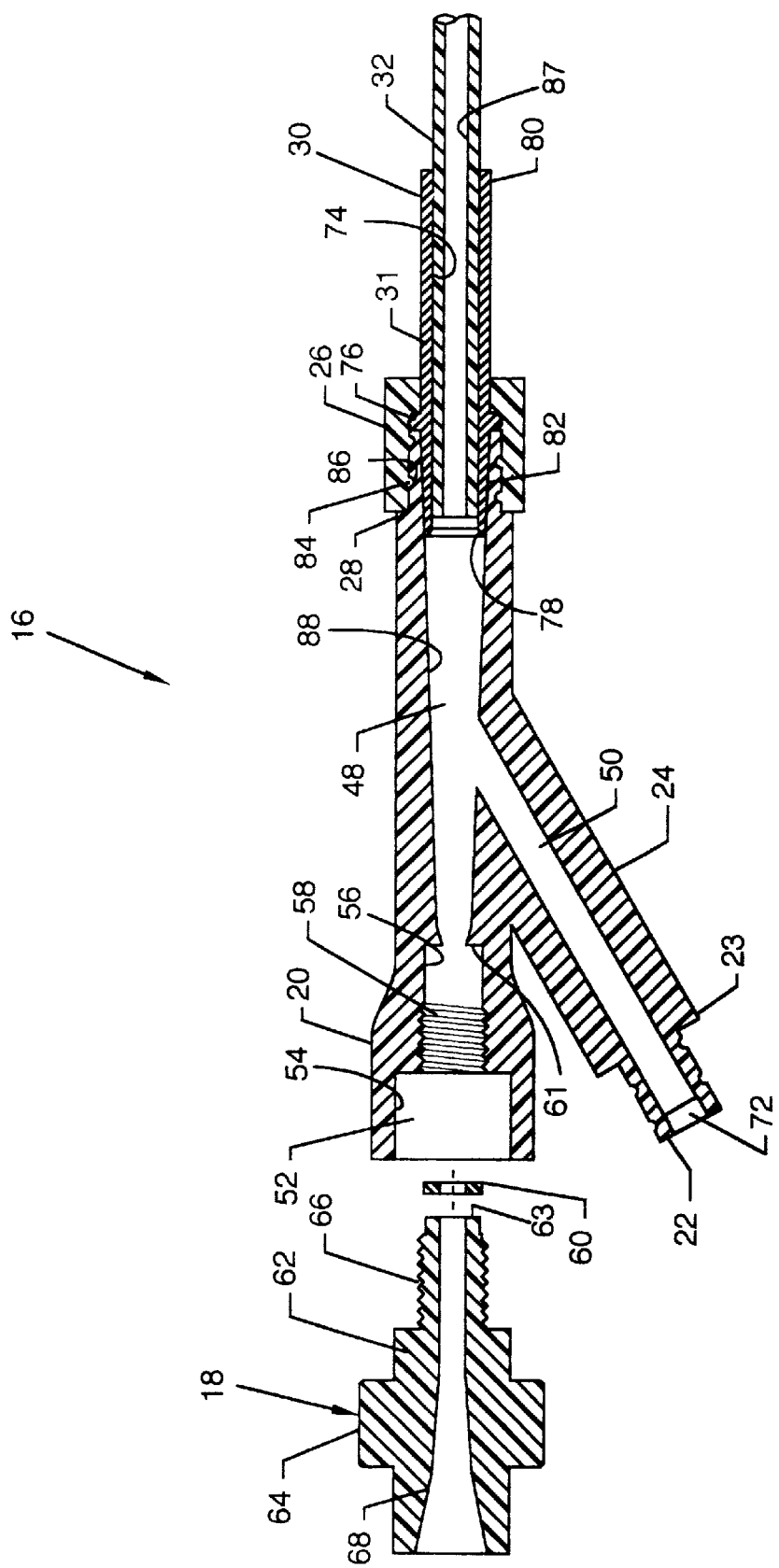
FIG. 3 is a semi-exploded cross sectional side view of a manifold and adjacent components constituting parts of the outer assembly.

FIG. 3 illustrates a semi-exploded cross sectional side view of the manifold 16 and adjacent components, where all numerals correspond to those elements previously or otherwise described. The manifold 16 includes a tapered centrally located passage 48 aligned along the longitudinal axis of the manifold 16 and a branch passage 50 extending along the axis of the branch 24 which intersects and is connected to the central passage 48. The manifold proximal end 20 houses a multi-radius cavity 52 including a round outer cavity portion 54 and a connected round inner and smaller cavity portion 56 having a threaded surface 58 on the proximal portion thereof. The hemostasis nut 18 includes a body 62 having a grasping surface 64 extending thereabout, a threaded surface 66 extending from the body 62, an annular surface 63 at the end of the threaded surface 66, and a passageway 68 aligned centrally to the longitudinal axis of the hemostasis nut 18. The passageway 68 has a wide radius at the proximal end which decreases toward the distal end. The initial wide radius is helpful for insertion of the inner assembly 14 or guidewires and the like. A seal 60 aligns to the distally located annular surface 61 of the round inner cavity portion 56 and bears against the annular surface 63 of the hemostasis nut 18 to seal the central passage 48 of the manifold 16 to the passageway 68 in the hemostasis nut 18.

The multi-radius cavity 52 and its internal geometry accommodate corresponding geometry of the hemostasis nut 18 and the seal 60. Luer connection 22 extends from the angled manifold branch proximal end 23. A filter 72 aligns at the mouth of the branch passage 50. The filter 72 and a Luer fitting (not illustrated) can be used to prevent any particulate outflow, to provide for metered outflow, or, alternatively, to provide suction for fluid or particle evacuation.

Luer fitting 26 is utilized to secure the strain relief 30 and the catheter 32 to the distal manifold end 28. The strain relief 30 is comprised of a tube 31, a central bore 74 internal to the tube 31 which accommodates the catheter 32, an annular flange 76 about the tube 31, and a tapered proximal tube mouth end 78. It is noted that the outer diameter of the tube 31 is constant from the annular flange 76 to the distal tube end 80, and that the outer diameter steadily decreases from the annular flange 76 to the tapered proximal tube mouth end 78 to provide a tapered tube surface 82 which conforms, for purpose of a proper fit, to the taper of the tapered central passage surface 88 of the central passage 48. The tapered proximal tube mouth end 78 allows for easily accomplished alignment of guidewires and other assemblies, such as inner assembly 14 and the like, with a lumen 87 located in the catheter 32. The Luer fitting 26 includes threads 84 which threadingly engage corresponding threads 86 at the distal end 28 of the manifold 16. The Luer fitting 26 bears against the annular flange 76 of the strain relief 30 to force the tapered tube surface 82 of the strain relief 30 against the tapered central passage surface 88 of the central passage 48 to effect a suitable seal.

Figure 4:
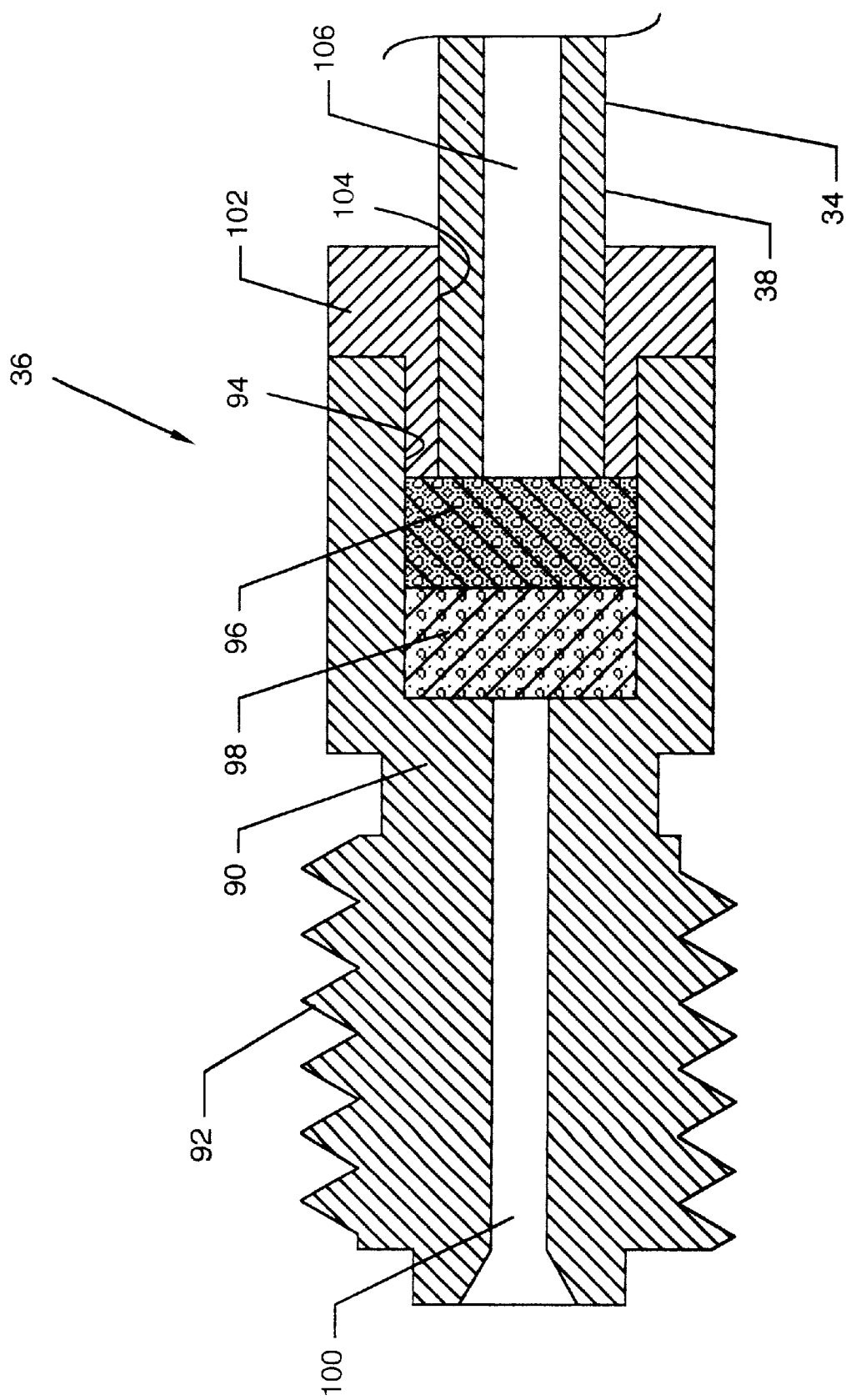
FIG. 4 is a longitudinal sectional view of a filter housing/high pressure connection assembly attached to the proximal end of a hypo-tube, shown only partially.

FIG. 4 illustrates a longitudinal sectional view of the filter housing/high pressure connection assembly 36 located at the hypo-tube proximal end 38 of the hypo-tube 34, where all numerals correspond to those elements previously or otherwise described. The filter housing/high pressure connection assembly 36 includes a cylindrical-like body 90 having a threaded surface 92, a tubular cavity 94, fine and course filters 96 and 98 residing in the tubular cavity 94, a central passage 100 extending through the body 90 and connecting to the tubular cavity 94, and a plug-like cap 102, having a central bore 104, extending into the tubular cavity 94 of the body 90. The hypo-tube 34 suitably secures within the central bore 104 of the cap 102. The central passage 100 communicates through fine and course filters 96 and 98 with the lumen 106 of the hypo-tube 34.

Figure 5:
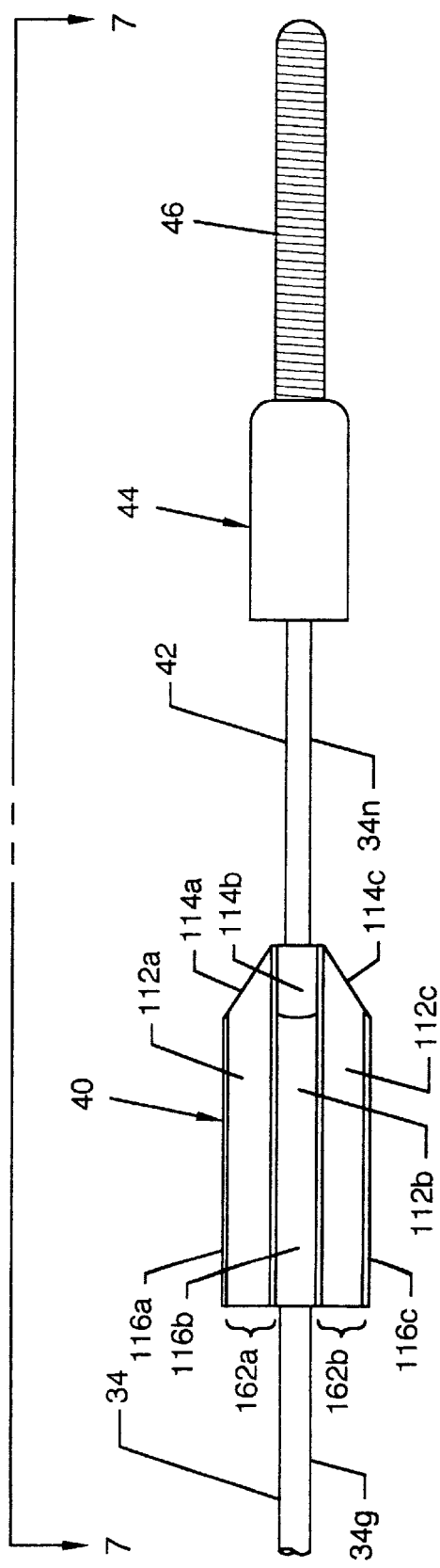
FIG. 5 is a side view of a transitional stop, a jet cap, and a guidewire coil aligned over and about the hypo-tube at the distal end thereof.

FIG. 5 illustrates a side view of the transitional stop 40, the jet cap 44 and the guidewire coil 46 aligned over and about the hypo-tube 34 near or at the hypo-tube distal end 42, where all numerals correspond to those elements previously or otherwise described. The relative sizes of the transitional stop 40 and the jet cap 44 with respect to each other and with respect to the sizes of the lumen 87 of the catheter 32 and a stationary stop 150 residing in the catheter 32, as well as details of the transitional stop 40, are discussed in detail below with relation to FIGS. 6, 12 and 13.

Figure 6:
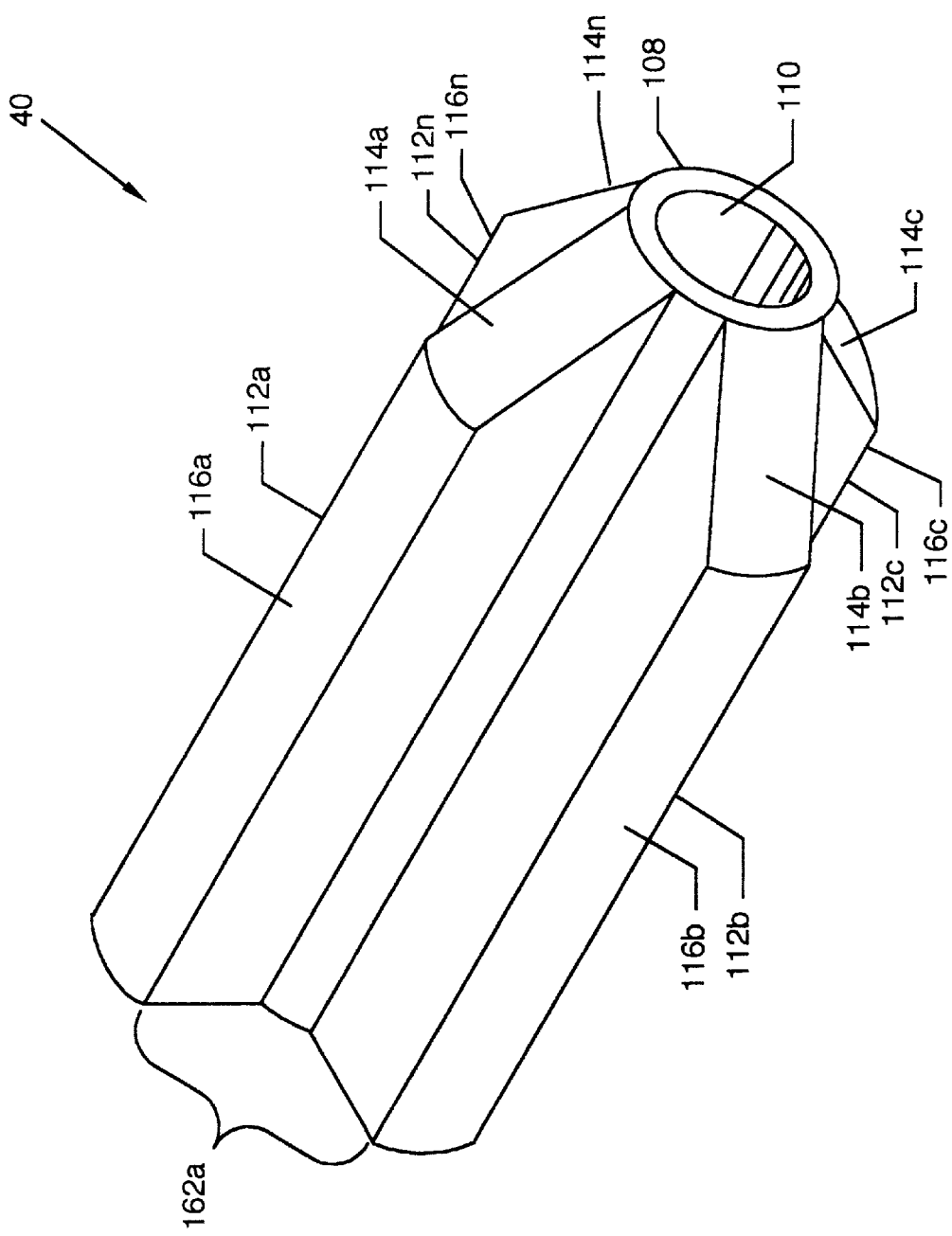
FIG. 6 is an isometric view of the transitional stop.

FIG. 6 illustrates an isometric view of the transitional stop 40, where all numerals correspond to those elements previously or otherwise described. The one-piece transitional stop 40 includes a tubular body 108 having a central bore 110 and a plurality of guide bars 112a–112n extending radially from the tubular body 108. Guide bars 112a–112n include angled leading edges 114a–114n extending from the leading portion of the body 108 to arced surfaces 116a–116n. The angled leading edges 114a–114n contact a stationary stop 150 in the catheter 32, as later described in detail. Preferably, and for purposes of example and illustration, the arced surfaces 116a–116n describe arcs centered on the longitudinal axis of the tubular body 108; but, in the alternative, the arced surfaces 116a–116n could describe arcs having other centers, or the surfaces could be flat or be of other geometric design, and shall not be construed to be limiting to the scope of the invention.

Figure 7:
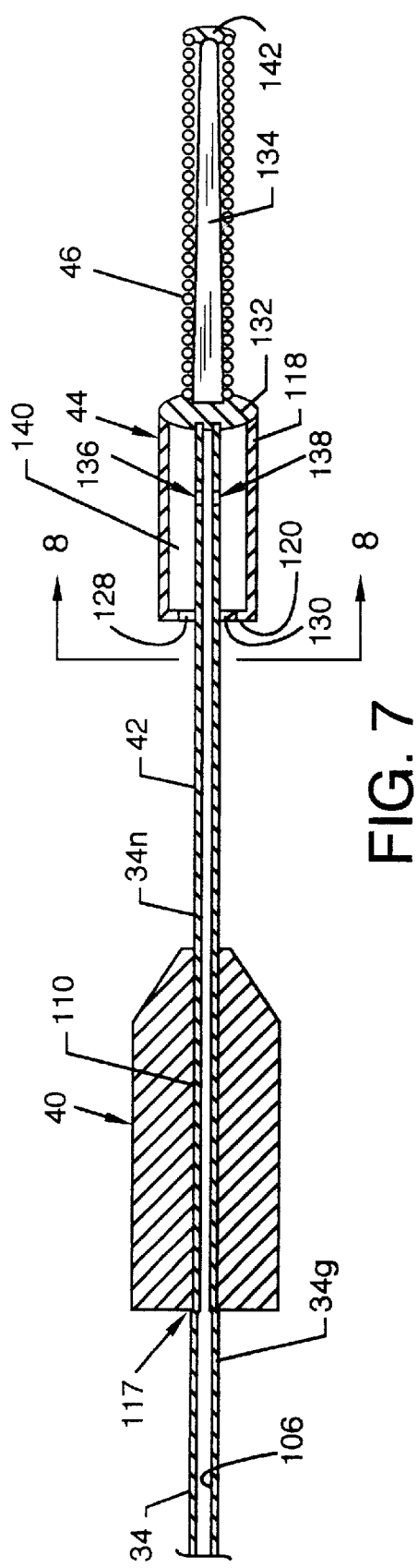
FIG. 7 is a longitudinal sectional view taken along line 7—7 of FIG. 5.
Figure 8:
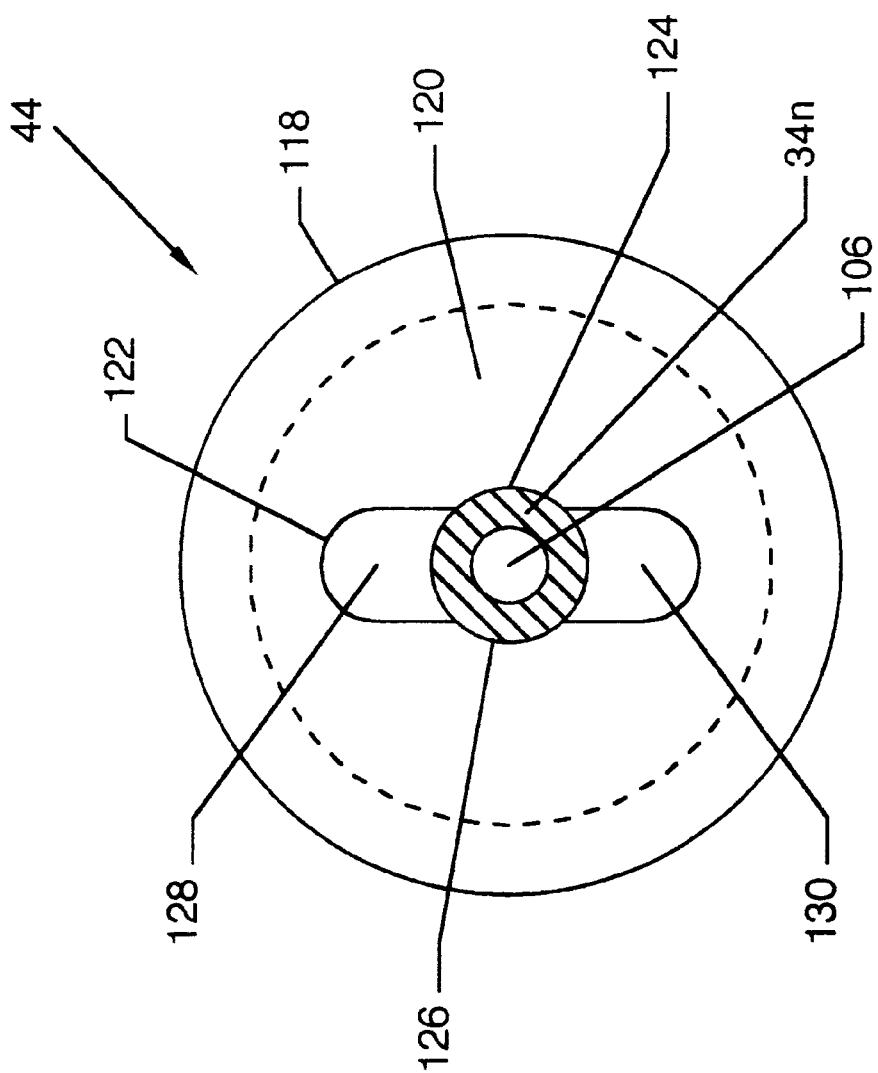
FIG. 8 is a view of the proximal end of the jet cap on the hypo-tube looking in the direction of line 8—8 of FIG. 7, with the hypo-tube shown in cross section.

FIG. 7 illustrates a longitudinal sectional view, taken along line 7–7 of FIG. 5, of the transitional stop 40, the jet cap 44 and the guidewire coil 46 aligned and secured over and about the hypo-tube 34 near or at the hypo-tube distal end 42; and FIG. 8 illustrates a view of the jet cap 44 looking in the direction of line 8–8 of FIG. 7, where all numerals correspond to those elements previously or otherwise described. The central bore 110 of the transitional stop 40 is aligned and appropriately secured over and about the last hypo-tube portion 34n to affix the transitional stop 40 over and about and near the hypo-tube distal end 42. The proximal end of the transitional stop 40 juxtaposes and abuts the shoulder-like transition 117 between the next to the last hypo-tube portion 34g and the last hypo-tube portion 34n. The jet cap 44 aligns over and about and is secured to the last hypo-tube portion 34n at the hypo-tube distal end 42. As shown in FIGS. 7 and 8, the jet cap 44 is tubular and includes a circular peripheral wall 118 and a circular end wall 120 extending inwardly from one end of the circular peripheral wall 118. Central to the circular end wall 120 is an elongated hole 122 having arcuate ends and opposite sides each having an arcuate mid section and straight portions extending oppositely from the arcuate mid section to the opposite arcuate ends, as shown in FIG. 8. The arcuate mid sections of the opposite sides of the elongated hole 122 are positioned at the center of the elongated hole 122 and are defined by opposing aligned arcuate portions 124 and 126 of common radius. The last hypo-tube portion 34n aligns to and extends through the center of the elongated hole 122 and is embraced by the arcuate portions 124 and 126, thereby dividing the elongated hole 122 into two jet orifices 128 and 130, the jet orifice 128 being defined by the portion of elongated hole 122 to one side of the outer surface of the last hypo-tube portion 34n, and the jet orifice 130 being defined by the portion of elongated hole 122 to the other side of the outer surface of the last hypo-tube portion 34n. At the distal end of the circular peripheral wall 118 is a weld 132 which joins together the circular peripheral wall 118, the extreme tip of the distal end 42 of the hypo-tube 34, the guidewire coil 46 and a tapered core 134. A plurality of orifices including orifices 136 and 138 in the distal end 42 of hypo-tube 34 align within the central cavity 140 of the jet cap 44 for fluid communication from lumen 106 to the central cavity 140 and to the two jet orifices 128 and 130. A weld 142 is also included at the distal end of the guidewire coil 46 to secure the end of the tapered core 134 to the guidewire coil 46 and to provide for smooth entry into a vessel or other body cavity.

Figure 9:
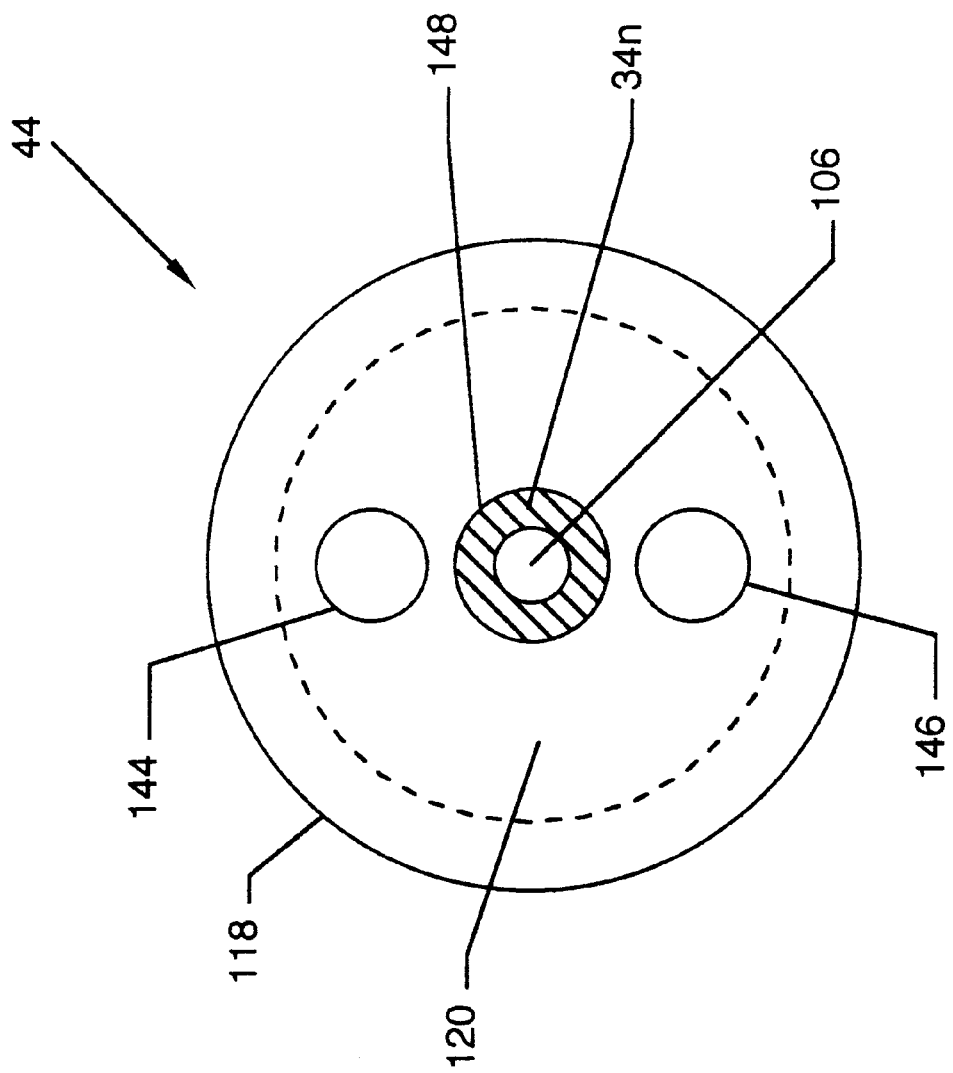
FIG. 9 is a view similar to FIG. 8 illustrating a slightly modified version of the et cap.

FIG. 9 illustrates a slightly modified version of the jet cap 44, wherein two distinct jet orifices 144 and 146 are included in the circular end wall 120 in lieu of the elongated hole 122 shown in FIG. 8, and wherein a bore 148 in the circular end wall 120 accommodates the last hypo-tube portion 34n.

Figure 10:
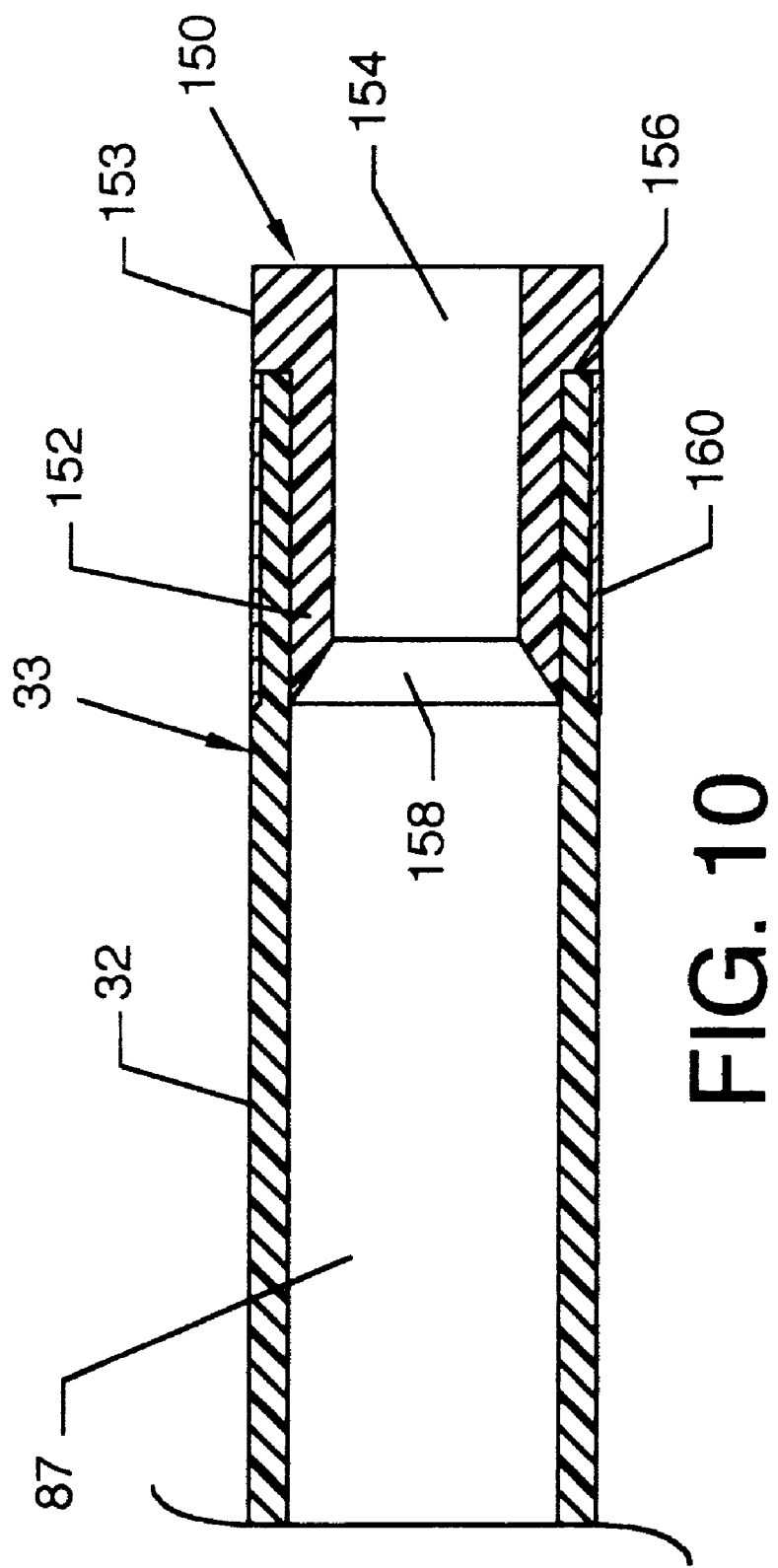
FIG. 10 is a longitudinal sectional view of the catheter distal end taken along line 10—10 of FIG. 2.

FIG. 10 illustrates a longitudinal sectional view of the catheter distal end 33 of the catheter 32 taken along line 10–10 of FIG. 2, where all numerals correspond to those elements previously or otherwise described. Illustrated in particular is the multi-radiused stationary stop 150 frictionally engaging the lumen 87 at the catheter distal end 33. One outer radius defines the cylindrical body 152, which frictionally engages lumen 87, and another larger outer radius defines a cap 153 at the end of the stationary stop 150. A central bore 154 aligns coaxially within the cylindrical body 152 and the cap 153. An annular shoulder 156 between the cap 153 and the cylindrical body 152 abuts and aligns to the catheter distal end 33. An angled annular surface 158, which is complementary to the angled leading edges 114a–114n of the transitional stop 40 shown in FIG. 6, is included at the proximal end of the cylindrical body 152. An annular crimp sleeve 160 applied over and about the catheter distal end 33 ensures a positive fixation of the stationary stop 150 in the lumen 87.

Figure 11:
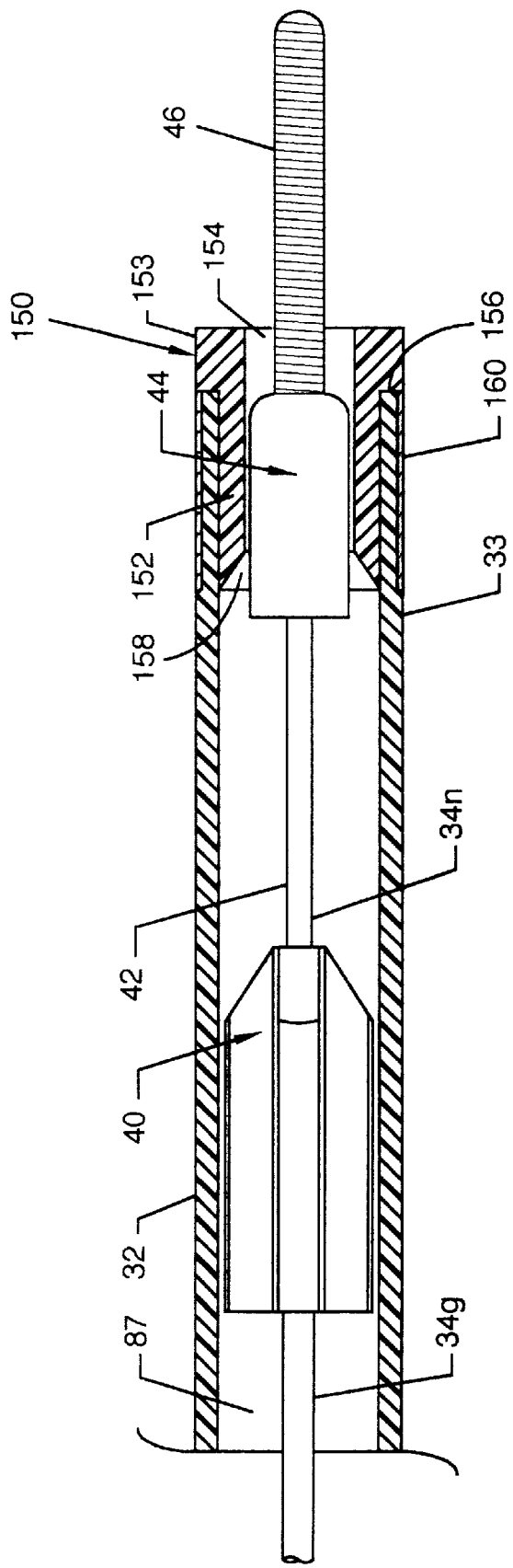
FIG. 11 is a longitudinal sectional view of the catheter distal end with the transitory stop, the jet cap, and the guidewire coil on the hypo-tube shown advancing therethrough.

FIG. 11 illustrates a longitudinal sectional view of the catheter distal end with the jet cap 44 transiting the central bore 154 of the stationary stop 150 and with the transitional stop 40 aligned within the lumen 87 of the catheter 32, where all numerals correspond to those elements previously or otherwise described.

Figure 12:
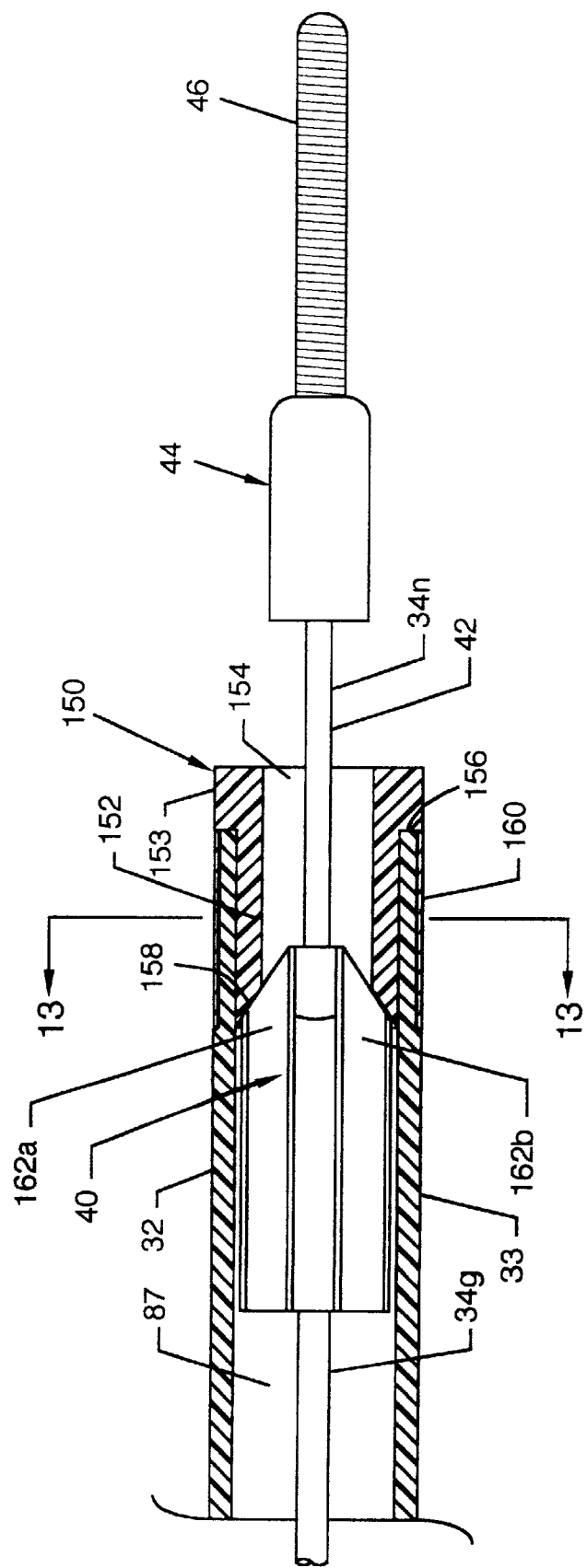
FIG. 12 is a longitudinal sectional view of the catheter distal end with the transitory stop, the jet cap, and the guidewire coil on the hypo-tube shown in final advanced position.

FIG. 12 illustrates a longitudinal sectional view of the catheter distal end with the transitional stop 40 aligned within the lumen 87 of the catheter 32 and in mutual engagement with the stationary stop 150, where all numerals correspond to those elements previously or otherwise described. Mutual engagement of the stationary stop 150 with the transitional stop 40 positions the jet cap 44 at a desirable and finite distance from the stationary stop 150 at the catheter distal end 33.

Tubular catheter 32 may be constructed of a flexible polymer material and is characterized by an ability to follow over a flexible guidewire through the vasculature of a patient to be treated. Since the tubular catheter 32 may also be subjected to reduced or vacuum pressures in some applications, the tubular catheter 32 should be resistant to collapse or bursting at the pressure differentials employed. Again, for purposes of example and illustration, the catheter 32 can have an outer diameter of about 0.040 inch or smaller, and an inner diameter of about 0.028 inch which can also taper in diameter. As is well known in the art, the catheter 32 may be advanced and maneuvered through the vasculature such that the catheter distal end 33 may be selectively positioned adjacent to the site of desired surgical action, for example, adjacent to a thrombus obstructing a blood vessel.

The stationary stop 150 may be formed from a variety of materials. Preferably, the stationary stop 150 is formed of material identical to that of the catheter 32.

The transitional stop 40 is mounted in the hypo-tube 34 at a location spaced apart from the hypo-tube distal end 42 and distal from the hypo-tube portion 34g. The transitional stop 40 has a cross sectional extent such that it may not freely pass the stationary stop 150. The transitional stop 40 has a substantially X-shaped cross section when viewed axially, as in FIG. 13, which allows for fluid passage in a proximal direction. However, as will be discussed subsequently, numerous alternative shapes might be employed for the transitional stop 40 provided that at least passage of the transitional stop past the stationary stop 150 is prevented. Preferably, the distal portion of the transitional stop 40 includes tapered surfaces, such as angled leading edges 114a–114n. The jet cap 44 presents a cross section capable of passing through the central bore 154 of the stationary stop 150. The angled leading edges 114a–114n serve, in juxtaposition with the angled annular surface 158 of the stationary stop 150, to desirably longitudinally position the transitional stop 40 relative to the stationary stop 150. The close longitudinal alignment of the plurality of guide bars 112a–112n within the lumen 87 of the catheter 32 generates lateral spaced relations, such as, for example, a concentric relationship between the first tube or catheter 32 and the second tube or hypo-tube 34, respectively. Preferably, the cross sectional extent of the transitional stop 40 is roughly about 0.010 inch to about 0.028 inch; however, the critical consideration in cross sectional dimensions of the transitional stop 40 is that it must pass through the lumen 87 of the first tube or catheter 32 and yet not pass the stationary stop 150.

The jet cap 44 is mounted at the distal end 42 of the hypo-tube 34 and includes a guidewire coil 46 extending distally from the jet cap 44. In a preferred embodiment, the jet cap 44, guidewire coil 46 and transitional stop 40 are radially symmetrical about the longitudinal extent of the hypo-tube 34. In such an embodiment, the jet cap 44 preferably has a diameter of from about 0.010 inch to about 0.030 inch. The hypo-tube 34 preferably has an outer diameter of about 0.008 inch to about 0.018 inch and also includes a continuous high pressure lumen 106 extending from the hypo-tube proximal end 38 to the hypo-tube distal end 42 and continuing into the jet cap 44. When the hypo-tube distal end 42 of the hypo-tube 34 is advanced through the lumen 87 of the catheter 32, the guidewire coil 46 and the jet cap 44 and any portion of the hypo-tube 34 distal from the transitional stop 40 are free to pass the location of the stationary stop 150. However, passage of the transitional stop 40 is prevented by the partial obstruction of the lumen 87 of catheter 32 by the stationary stop 150. Thus, when the distal angled leading edges 114a–114n of the transitional stop 40 engage the angled annular surface 158 of the stationary stop 150, a desired longitudinal relationship is dependably generated between the jet cap 44 and the catheter distal end 33 (at the cap 153) of the catheter 32. Most importantly, the jet cap 44 is oriented and spaced apart and distally situated at a desired relationship to the catheter distal end 33 of the catheter 32.

The jet cap 44 is preferably rounded or tapered at the distal end to facilitate advancement of the hypo-tube 34 and to avoid catching or snagging on the interior of the catheter 32, on the stationary stop 150, or on a vessel wall when advanced beyond the catheter distal end 33.

Fluid communication between the lumen 87 and the central bore 154 of the stationary stop 150 is allowed longitudinally and in a distal direction about the geometry of the transitional stop 40. As partially shown in FIGS. 5 and 6 and as fully shown in FIG. 13, longitudinally oriented passages 162a–116n are formed. For example, passage 162a is formed between guide bars 112a and 112b and a portion of the periphery of transitional stop body 108 extending from the proximal region of the transitional stop 40 distally toward and including the angled leading edges 114a–114b. Longitudinally oriented passages 162b–162n are formed in a corresponding fashion. Note particularly that a portion of the lumen 87 remains open where the transitional stop 40 interacts with the stationary stop 150 to allow passage of liquid and small portions of suspended tissue proximally through the catheter 32.

Figure 13:
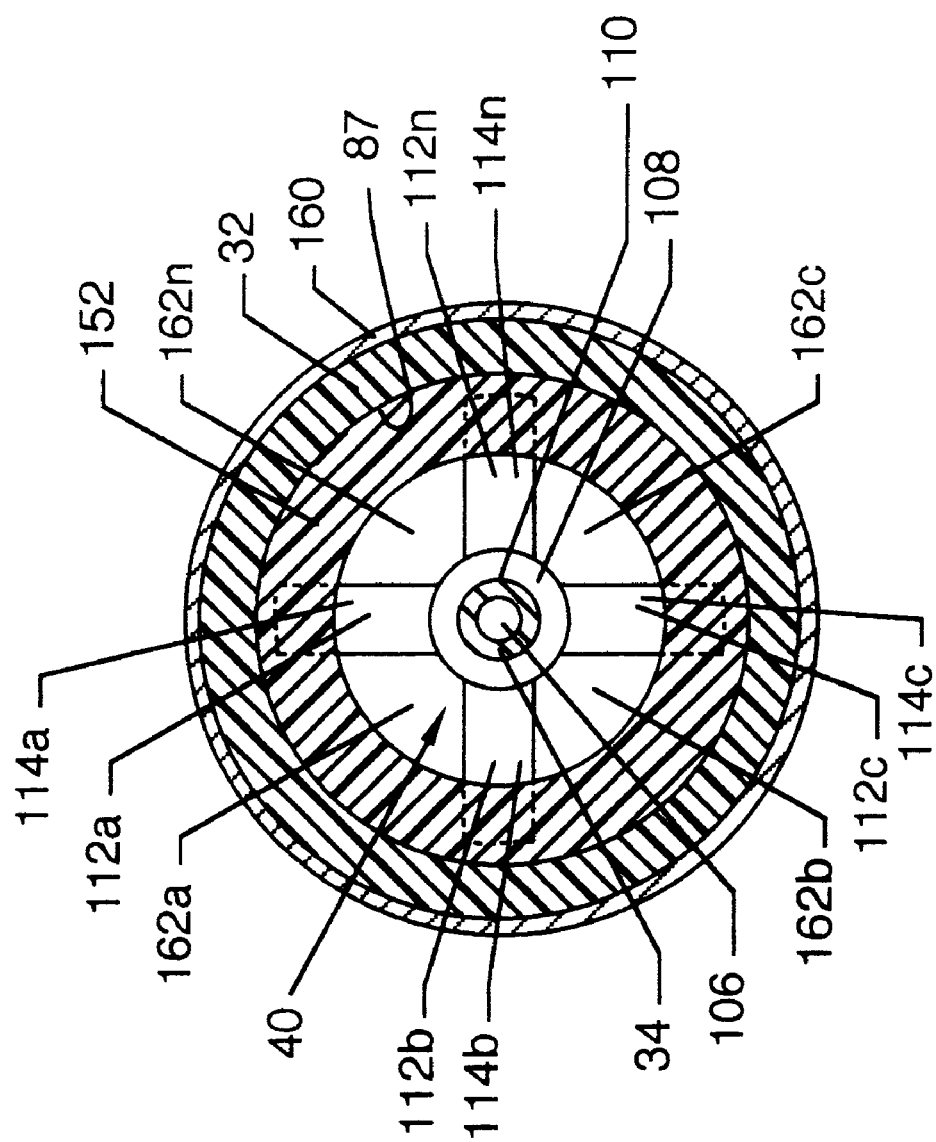
FIG. 13 is a cross-sectional view taken along line 13—13 of FIG. 12.

FIG. 13 illustrates a cross sectional view of the guide catheter distal end 33 taken along line 13—13 of FIG. 12, where all numerals correspond to those elements previously or otherwise described. Illustrated in particular are the plurality of passages 162a–162n about the transitional stop 40 which allow passage of liquid and small portions of suspended tissue proximally through the lumen 87 of the catheter 32. Although the guide bars 112a–112n include planar side surfaces, other configurations having a rounded intersection or even having non-planar intersecting walls or other variations of longitudinal passages can be utilized and shall not be construed to be limiting to the scope of the invention.

MODE OF OPERATION

Figure 14:
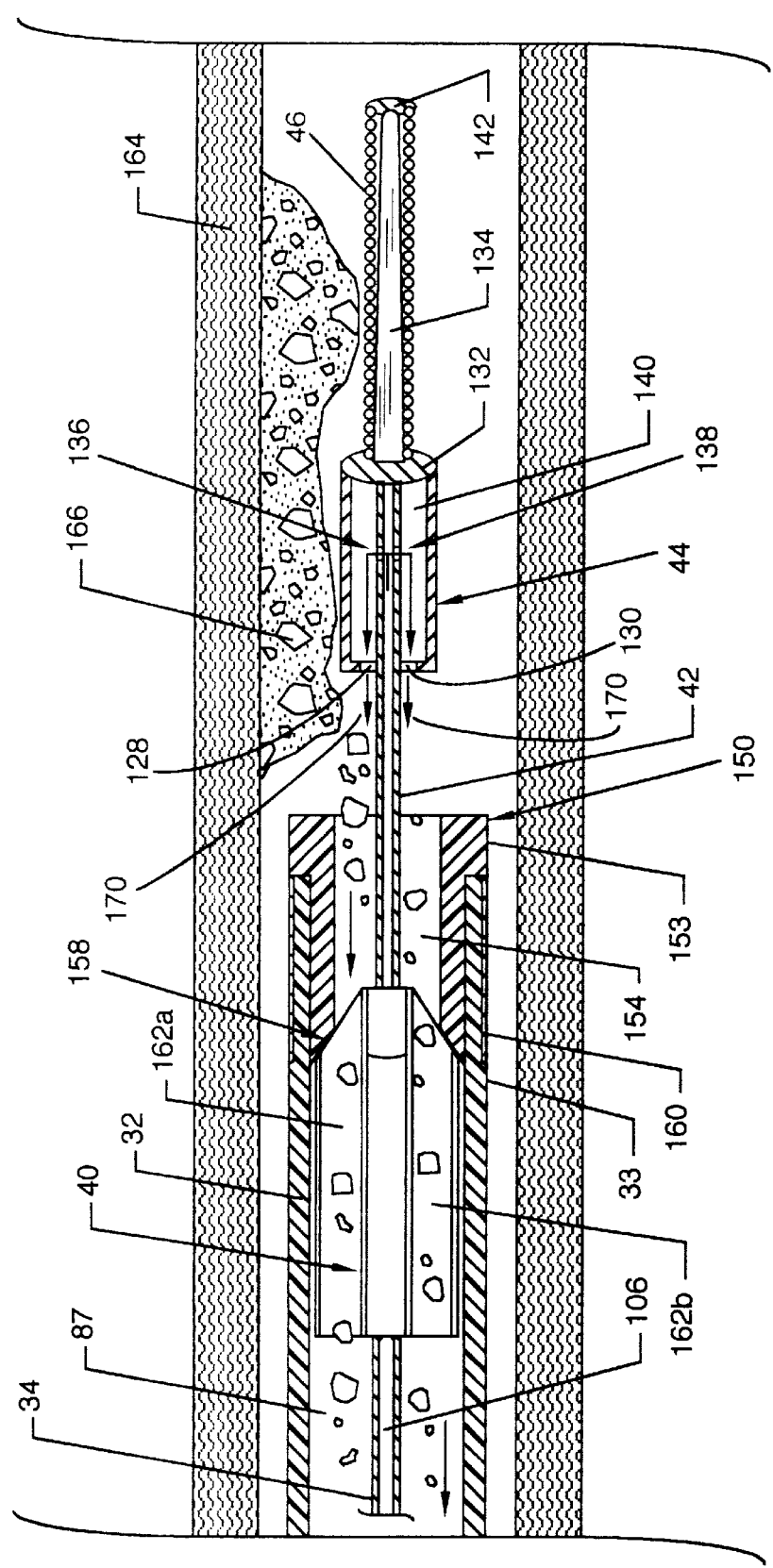
FIG. 14 is presented to illustrate schematically the mode of operation of the rheolytic thrombectomy catheter, and is a longitudinal sectional view depicting the distal end of the rheolytic thrombectomy catheter within a blood vessel at the site of a thrombotic deposit and lesion.

FIG. 14 best illustrates the mode of operation of the rheolytic thrombectomy catheter 10 with particular attention to the catheter distal end 33 and jet cap 44 positioned in a blood vessel 164, artery or the like at the site of a thrombotic deposit and lesion 166.

A guidewire is first advanced percutaneously through the vasculature to the site of the thrombotic deposit and lesion 166. For a distal coronary vessel or a vessel of the brain, typically the guidewire has a diameter of 0.010–0.016 inch. This invention can also be applied to larger vessels which require larger diameter guidewires. Once a guidewire has been advanced along the vessel 164 and has reached the thrombotic deposit and lesion, catheter 32, the first tube, which serves as a flexible evacuation tube, can be advanced over the guidewire through tortuous turns to reach the thrombotic deposit and lesion. With the catheter distal end 33 of the catheter 32 positioned near the thrombotic deposit and lesion 166, the guidewire can then be removed from the catheter 32 and the patient's body. The jet cap 44 at the terminus of the second tube or hypo-tube 34 is then advanced within the lumen 87 of the catheter 32 until the transitional stop 40 contacts the stationary stop 150 of the catheter 32.

The arced surfaces 116a–116n at the extremities of the guide bars 112a–112n of the transitional stop 40 provide for guidance of the transitional stop 40 along the lumen 87 and also center the jet cap 44 in the center of the catheter 32 during initial transition and provide for centering of the jet cap 44 in the central bore 154 of the stationary stop 150 prior to engagement of the transitional stop 40 with the stationary stop 150. Engagement of the angled leading edges 114a–114n with the stationary stop 150 sets a predetermined gap or distance from the jet cap 44 proximal end to the stationary stop 150. The central bore 154 and lumen 87 of the catheter 32 serve as an evacuation tube at the catheter distal end 33. The rheolytic thrombectomy catheter 10 can then be activated by providing high pressure liquid, preferably saline, to the proximal end of the catheter 32 via the manifold 16.

High pressure saline, or other liquid, from the manifold 16 is provided and flows through the lumen 106 of the hypo-tube 34 to exit orifices 136 and 138 leading to the central cavity 140 of the jet cap 44. The high pressure saline exits jet orifices 128 and 130 as retrograde jets 170 of high velocity saline being directed toward the open central bore 154 in the stationary stop 150 at the catheter distal end 33. The high velocity saline jets 170 dislodge tissue from the thrombotic deposit and lesion 166 and entrain it into the saline jets 170 where it is broken up into smaller fragments. Impingement of the saline jets 170 onto the catheter distal end opening creates a stagnation pressure within the evacuation lumen 87 that drives the debris particles of tissue from the thrombotic deposit and lesion 166 toward the proximal end of the catheter 32.

A positive displacement piston pump (not illustrated) can be used to provide liquid, preferably saline, under pressure to the proximal end of the hypo-tube 34. A pressure ranging from 500–15,000 psi will provide the energy to create a useful high velocity jet as the saline exits the jet orifices 128 and 130 located at the circular end wall 120 of the jet cap 44. The flow rate of saline can be controlled by adjusting the pumping rate of the positive displacement pump. The proximal end of the catheter 32 interfaces with a suction device through the Luer connection 22 at the manifold branch 24, for example, a roller pump, prior to discharge of the evacuated thrombotic debris into a collection bag for disposal. The rate of evacuation can be controlled by adjusting the rate of the roller pump. The rate of saline inflow can be balanced with the rate of removal of thrombotic debris by simultaneous adjustment of the piston pump and the roller pump. The rate of saline inflow can be less than, equal to, or greater than the rate of removal of thrombotic debris. The rate of thrombus removal can be set to slightly exceed the rate of saline inflow to reduce the likelihood for distal embolization of thrombotic tissue.

ALTERNATIVE EMBODIMENTS

Figure 15:
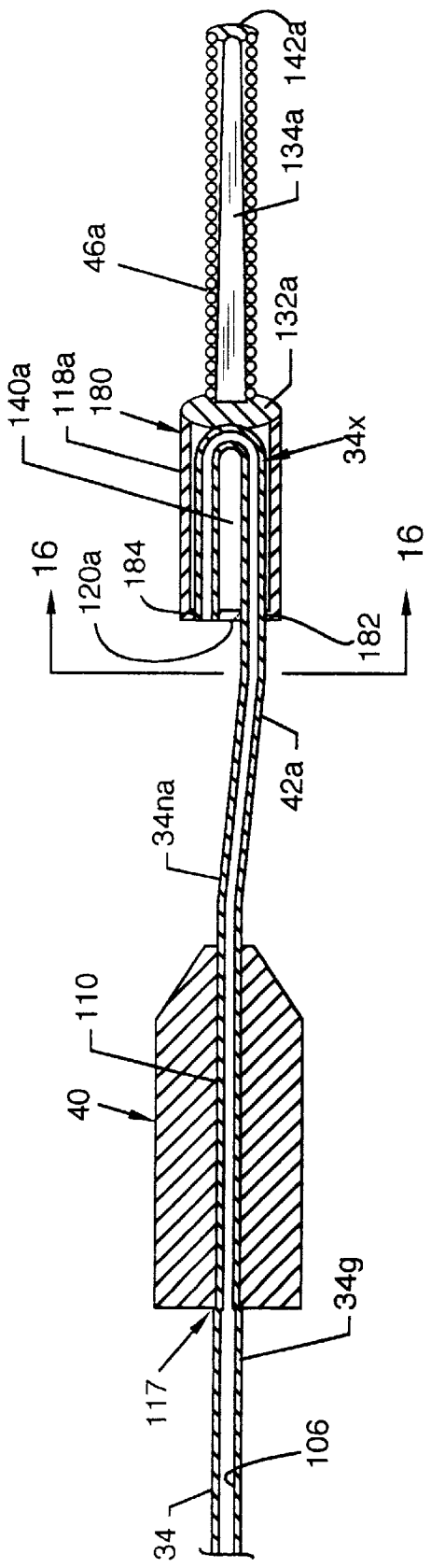
FIG. 15 is a longitudinal sectional view similar to FIG. 7 but illustrating an alternative jet cap embodiment.
Figure 16:
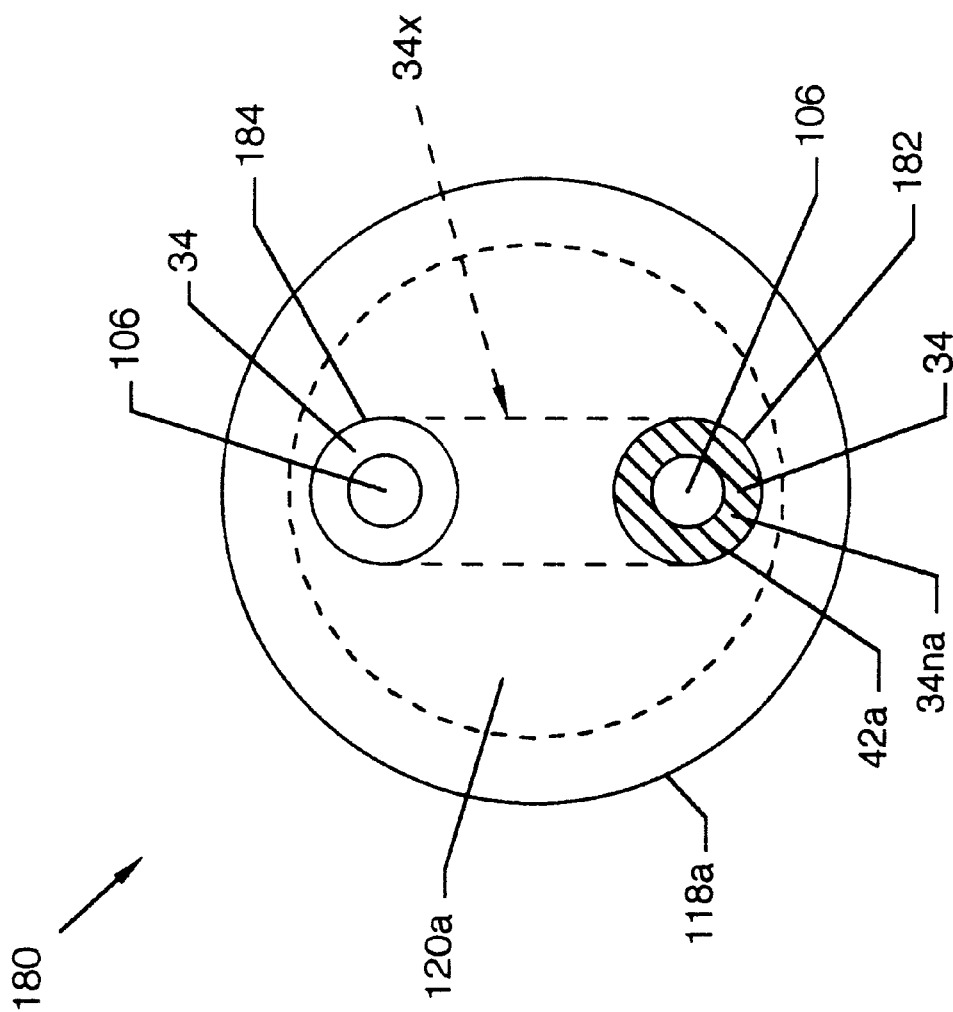
FIG. 16 is a view the proximal end of the alternative jet cap embodiment shown in FIG. 15 looking in the direction of line 16—16 of FIG. 15, with the hypo-tube shown in cross section.

FIG. 15, a first alternative embodiment, illustrates a longitudinal sectional view of the transitional stop 40, an alternative jet cap 180, in lieu of jet cap 44, and a guidewire coil 46a aligned and secured over and about the hypo-tube 34 near or at a hypo-tube distal end 42a; and FIG. 16 illustrates a view of the jet cap 180 looking in the direction of line 16-16 of FIG. 15, where all numerals correspond to those elements previously or otherwise described. The jet cap 180 includes several like components as described previously. The jet cap 180 aligns over and about and is secured to the last hypo-tube portion 34na, which angles downwardly from the longitudinal axis of the hypo-tube 34 at the hypo-tube distal end 42a. The jet cap 180 is tubular and includes a circular peripheral wall 118a and a circular end wall 120a extending inwardly from one end of the circular peripheral wall 118a. Located in the circular end wall 120a are two holes 182 and 184 which support a U-shaped hypo-tube portion 34x extending from the last hypo-tube portion 34na. The U-shaped hypo-tube portion 34x aligns to and extends through the holes 182 and 184 in the circular end wall 120a, as well as through the jet cap central cavity 140a. The free end portion of the U-shaped hypo-tube portion 34x secures in the hole 184 flush with the circular end wall 120a and is open, thereby defining an orifice aligned to direct a high velocity jet stream, preferably saline, in a proximal direction in a manner and fashion such as previously described. At the distal end of the circular peripheral wall 118a is a weld 132a which joins together the circular peripheral wall 118a, the bight of the U-shaped portion 34x of the hypo-tube 34, the guidewire coil 46a and a tapered core 134a. A weld 142a is also included at the distal end of the guidewire coil 46a to secure the end of the tapered core 134a to the guidewire coil 46a and to provide for smooth entry into a vessel or other body cavity.

FIG. 16 is a view of the proximal end of the first alternative jet cap embodiment looking in the direction of line 16–16 of FIG. 15, where all numerals correspond to those elements previously or otherwise described.

Figure 17:
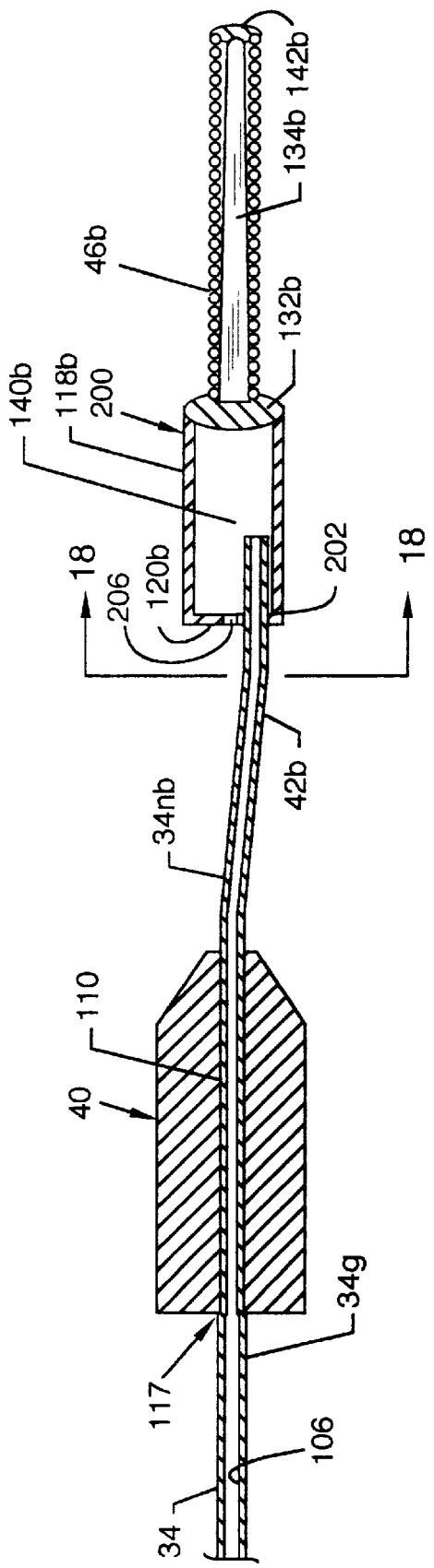
FIG. 17 is a longitudinal sectional view similar to FIG. 15 but illustrating another alternative jet cap embodiment.
Figure 18:
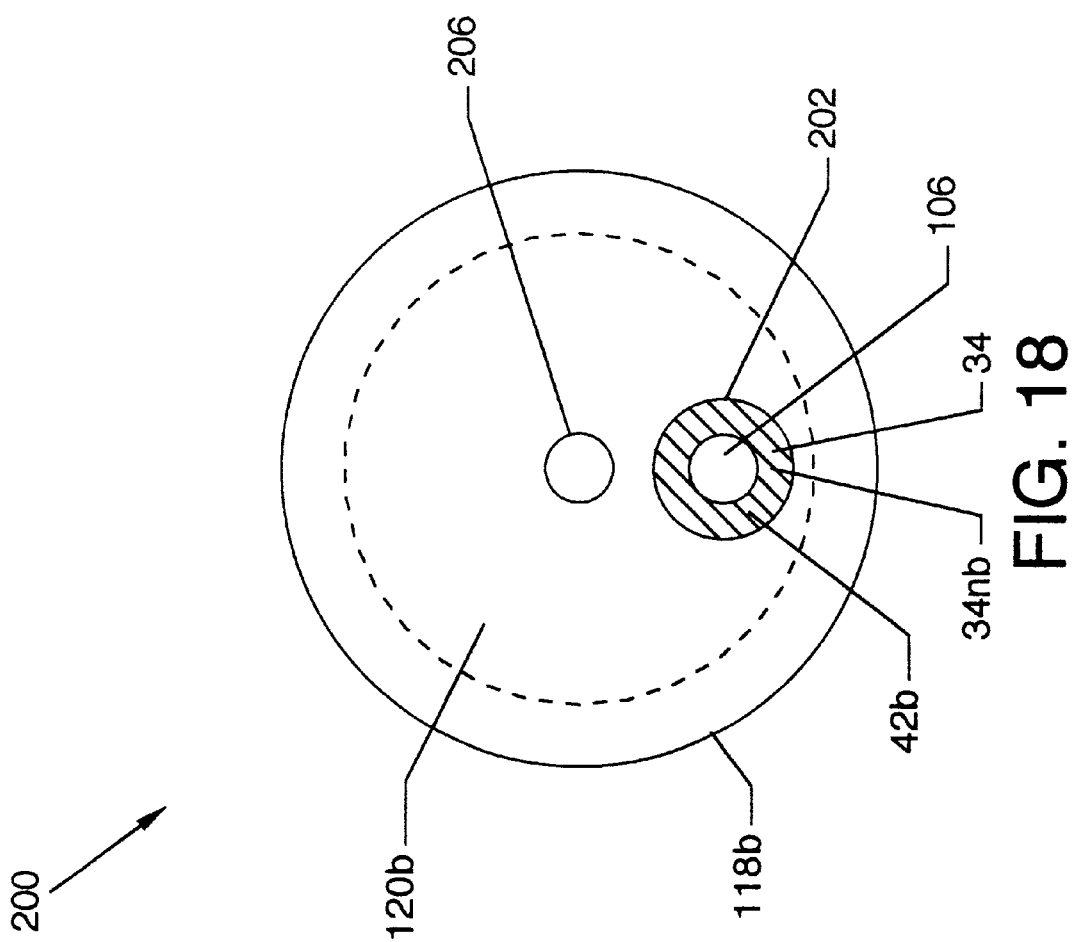
FIG. 18 is a view of the proximal end of the alternative jet cap embodiment shown in FIG. 17 looking in the direction of line 18—18 of FIG. 17, with the hypo-tube shown in cross section.

FIG. 17, a second alternative embodiment, illustrates a longitudinal sectional view of the transitional stop 40, an alternative jet cap 200, in lieu of jet cap 44, and a guidewire coil 46b aligned and secured over and about the hypo-tube 34 near or at a hypo-tube distal end 42b; and FIG. 18 illustrates a view of the jet cap 200 looking in the direction of line 18-18 of FIG. 17, where all numerals correspond to those elements previously or otherwise described. The jet cap 200 includes several like components as described previously. The jet cap 200 aligns over and about and is secured to the last hypo-tube portion 34nb, which angles downwardly from the longitudinal axis of the hypo-tube 34 at the hypo-tube distal end 42b. The jet cap 200 is tubular and includes a circular peripheral wall 118b and a circular end wall 120b extending inwardly from one end of the circular peripheral wall 118b. Located in the circular end wall 120b is a hole 202, and, preferably, a centrally located jet orifice 206. Preferably one jet orifice is included, although more jet orifices can be utilized and shall not be deemed as limiting to the scope of the invention. The last hypo-tube portion 34nb aligns to and extends through the hole 202 in the circular end wall 120b and has an open end or orifice which ends in the jet cap central cavity 140b of the jet cap 200 for fluid communication from lumen 106 to the central cavity 140b and to the jet orifice 206 to direct a high velocity jet stream, preferably saline, in a proximal direction in a manner and fashion such as previously described. At the distal end of the circular peripheral wall 118b is a weld 132b which joins together the circular peripheral wall 118b, the guidewire coil 46b and a tapered core 134b. A weld 142b is also included at the distal end of the guidewire coil 46b to secure the end of the tapered core 134b to the guidewire coil 46b and to provide for smooth entry into a vessel or other body cavity.

FIG. 18 is a view of the proximal end of the second alternative jet cap embodiment looking in the direction of line 18—18 of FIG. 17, where all numerals correspond to those elements previously or otherwise described.

Figure 19:
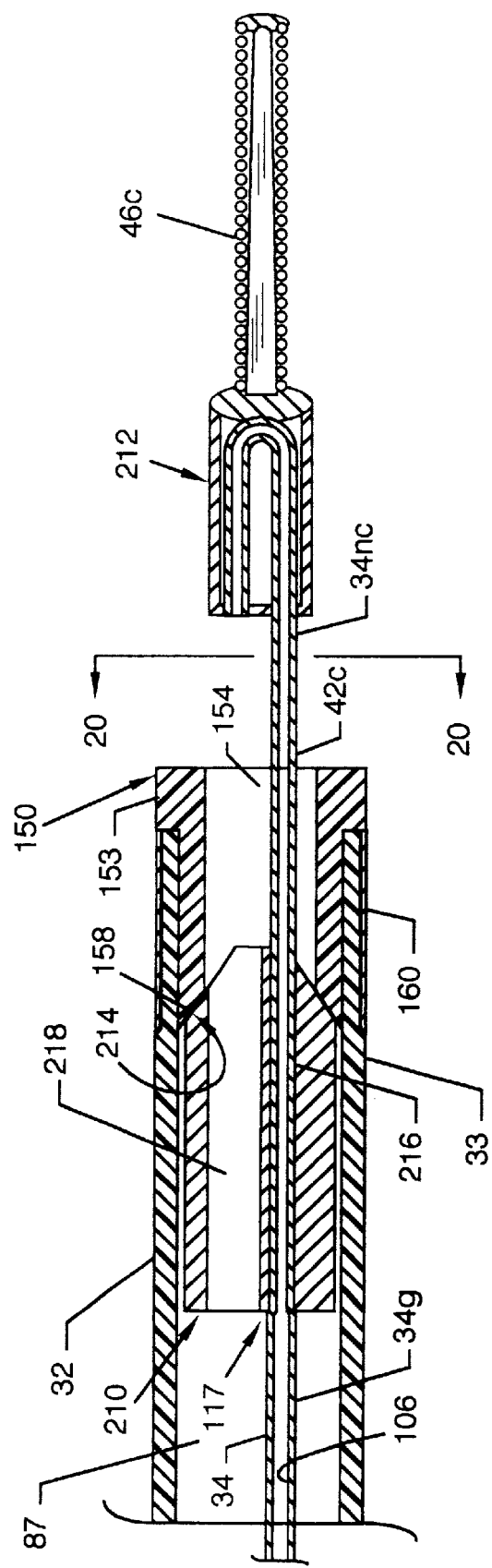
FIG. 19 is a longitudinal sectional view similar to FIG. 12 but illustrating an alternative transitional stop embodiment.

FIG. 19, a third alternative embodiment, illustrates a longitudinal sectional view of a transitional stop 210, a jet cap 212 being similar to the configuration of jet cap 180 of FIG. 15 and in lieu of jet cap 44, and a guidewire coil 46c, being similar in configuration to guidewire coil 46a, aligned and secured over and about the hypo-tube 34 near or at a non-angled hypo-tube distal end 42c; and PIG. 20 illustrates a view of the catheter distal end 33 looking in the direction of line 20—20 of PIG. 19, where all numerals correspond to those elements previously or otherwise described. In this embodiment the jet cap 212 aligns over and about and is secured to the last hypo-tube portion 34nc which projects straight outwardly from the lumen 87 and from transitional stop 210. The longitudinal axis of the hypo-tube 34 and the last hypo-tube portion 34nc is offset from the central axis of the transitional stop 210, at the hypo-tube distal end 42c. Having the last hypo-tube portion 34nc located off-center obviates the requirement of having a last hypo-tube portion which angles downwardly from the longitudinal axis of the hypo-tube 34 and also allows the jet cap 212 to align with the central bore 154 of the stationary stop 150 without having an angled last hypo-tube portion. The transitional stop 210 is fashioned of a solid material having a circular cross section, one end of which is in the form of a truncated cone having an angled annular surface 214 and also having a longitudinally oriented hole 216 distant from the central longitudinal axis of the transitional stop 210 and, in addition, a longitudinally oriented lumen 218 distant from the central longitudinal axis of the transitional stop 210. The transitional stop 210 is positioned as illustrated to position the angled annular surface 214 against the angled annular surface 158 of the stationary stop 150 to position the jet cap 212 at a desirable and finite distance from the stationary stop 150 at the catheter distal end 33 so that a high velocity jet stream, preferably saline, emanating from the open end or orifice of the hypo-tube may be directed in a proximal direction in a manner and fashion toward the lumen 218 to dislodge, break up and carry away thrombotic tissue debris, such as previously described.

Figure 20:
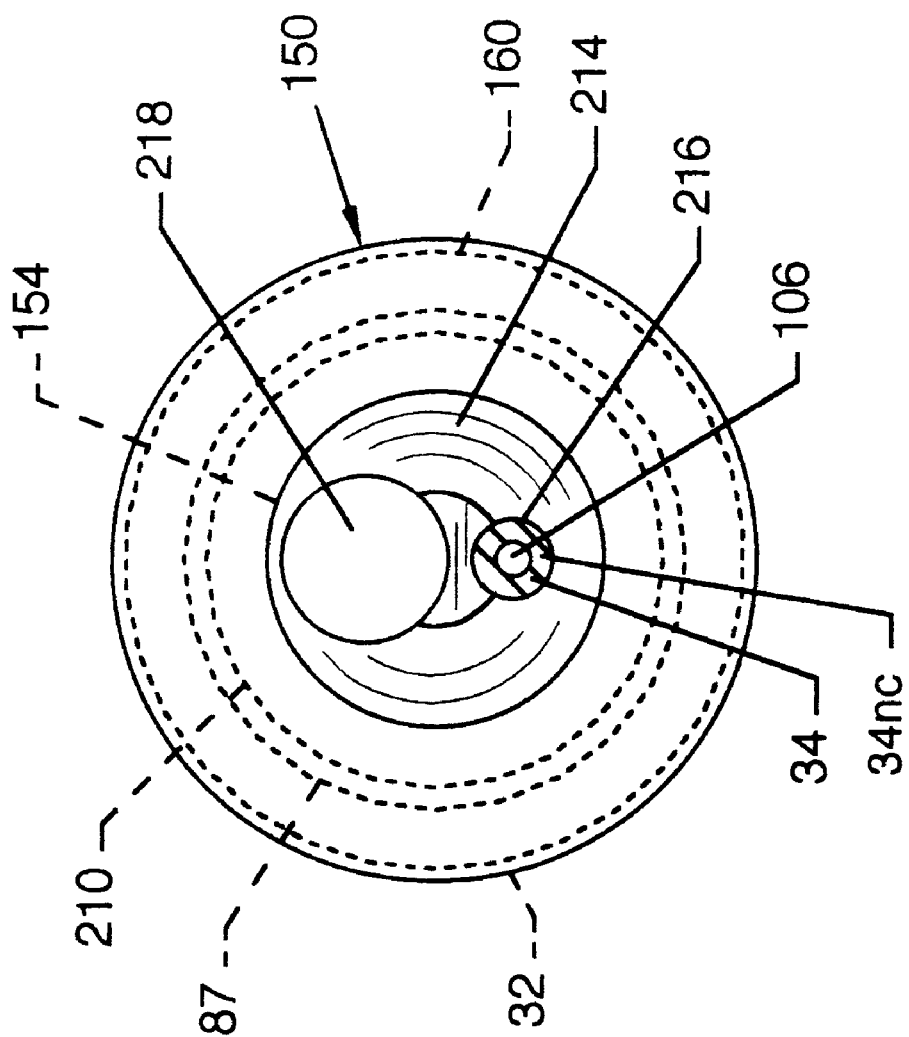
FIG. 20 is a view of the catheter distal end looking in the direction of line 20—20 of FIG. 19, with the hypo-tube shown in cross section.

FIG. 20 illustrates a view of the catheter distal end 33 looking in the direction of line 20—20 of FIG. 19, where all numerals correspond to those elements previously or otherwise described.

Figure 21:
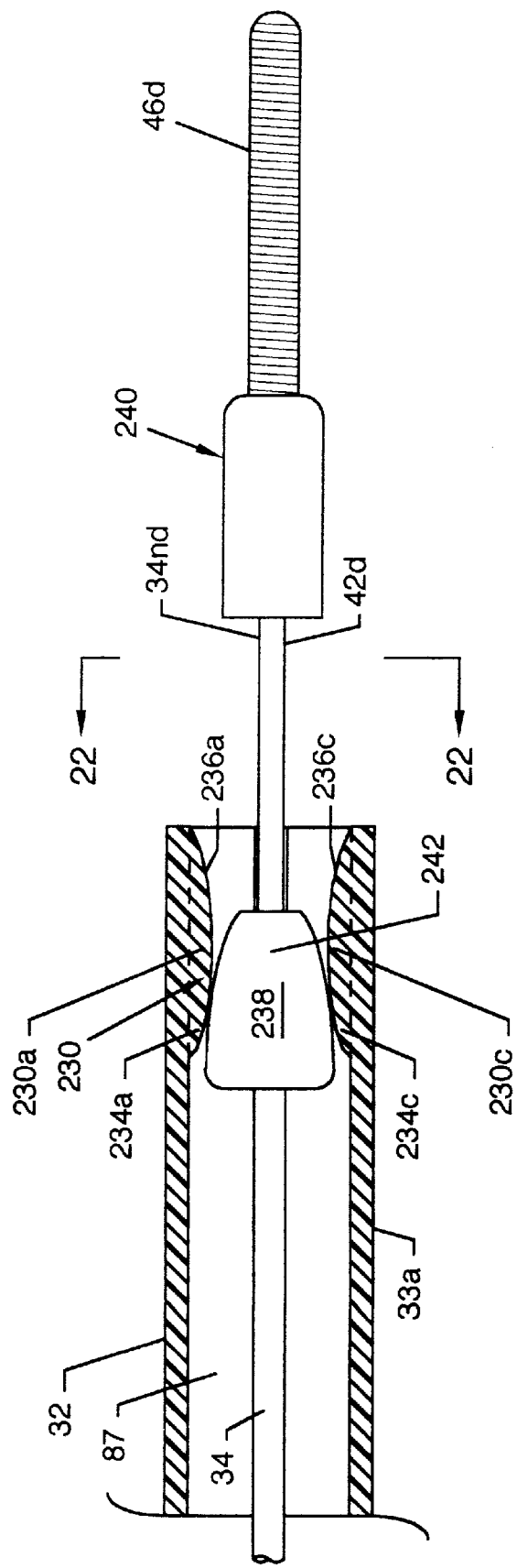
FIG. 21 is a view similar to FIG. 12 but illustrating alternative embodiments of the transitional stop and the stationary stop.

FIG. 21, a fourth alternative embodiment, illustrates a longitudinal sectional view of a catheter distal end 33a and having alternatively configured stationary and transitional stops, where all numerals correspond to those elements previously or otherwise described. Located at the catheter distal end 33a of the catheter 32 is a stationary stop 230. The stationary stop 230 is permanently connected to, molded to, or otherwise formed to the tubing wall of the catheter 32 and projects into the lumen 87 of the catheter 32. By projecting inward and into the lumen 87, the stationary stop 230, being comprised of a plurality of arcuate stops 230a–230n, partially obstructs the lumen 87. However, the stationary stop 230 does not fully obstruct the lumen 87. Moreover, the stationary stop 230 allows for free passage of a standard guidewire through the lumen 87 in the region adjacent the catheter distal end 33a of the catheter 32. Preferably, and for purposes of example and illustration, the arrangement and dimensions of the stationary stop 230 are such that a coronary or neurological guidewire having a diameter of at least 0.010 inch, more preferably 0.016 inch, can freely pass the stationary stop 230. Most preferably, the unobstructed diameter of the stationary stop 230 is from about 0.010 inch to about 0.030 inch. The catheter 32 has an outer diameter of about 0.040 inch and an inner diameter of about 0.028 inch or smaller. As is well known in the art, the catheter 32 may be advanced and maneuvered through the vasculature such that the catheter distal end 33a may be selectively positioned adjacent to the site of desired surgical action, for example, adjacent to a thrombus obstructing a blood vessel.

The stationary stop 230 has a plurality of arcuate stops 230a–230n aligned parallel to the central axis of the catheter 32, each having a proximal tapered surface 234a–24n and a distal tapered surface 236a–236n. The stationary stop 230 may be formed from a variety of materials. Preferably, the stationary stop 230 is formed of material identical to that of the catheter 32. Most preferably, the stationary stop 230 is fabricated by a permanent deformation and thickening of the wall of the catheter 32 at the desired location. Alternatively, the stationary stop 230 might be separately constructed and then fixed within the catheter 32.

The hypo-tube 34, or second tube, is fashioned as previously described having a hypo-tube distal end 42d and a proximal end (not shown). A transitional stop 238 is mounted on the last hypo-tube portion 34nd at a location spaced apart from a jet cap 240 and a guidewire coil 46d also mounted on the last hypo-tube portion 34nd. The transitional stop 238 has a cross sectional extent such that it may not freely pass the stationary stop 230. In one embodiment, the transitional stop 238 has a rounded cross section when viewed axially. However, numerous alternative shapes might be employed for the transitional stop 238 provided that at least passage past the stationary stop 230 is prevented. Preferably, the distal surface 242 of the transitional stop 238 is tapered, such that a distalmost extent of the transitional stop 238 presents a cross section capable of passing the proximalmost extent of the stationary stop 230, generally as represented by the proximal tapered surfaces 234a–234n. Distal tapered surface 242 serves a dual function by first facilitating passage and advancement of the hypo-tube 34 by reducing any tendency to catch or bind within the catheter 32, and second, to desirably laterally position the transitional stop 238 relative to the stationary stop 230 and thereby generate lateral relations, such as for example, a concentric relationship between the catheter 32 and hypo-tube 34, respectively. Preferably, the cross sectional extent of the transitional stop 238 is roughly about 0.010 inch to about 0.028 inch; however, the critical consideration in cross sectional dimensions of the transitional stop 238 is that it must pass through the lumen 87 of the catheter 32 and yet not pass the stationary stop 230.

As previously mentioned, a jet cap 240 is mounted at the hypo-tube distal end 42d of the hypo-tube 34. A guidewire coil 46d extends distally from the jet cap 240. The jet cap 240, guidewire coil 46 and transitional stop 238 are radially symmetrical about the longitudinal extent of the hypo-tube 34. The jet cap 240 preferably has a diameter of from about 0.010 inch to about 0.030 inch. The hypo-tube 34 preferably has an outer diameter of about 0.008 inch to about 0.018 inch and also includes a continuous high pressure lumen 106 extending from the proximal end to the hypo-tube distal end 42d and continuing into the jet cap 240. When the end of the hypo-tube 34 is advanced through the lumen 87 of the catheter 32, the guidewire coil 46d adjacent the jet cap 240 and any portion of the hypo-tube 34 distal from the transitional stop 238 are free to pass the location of the stationary stop 230. However, passage of the transitional stop 238 is prevented by the partial obstruction of the lumen 87 of catheter 32 by the stationary stop 230. Thus, when the distal tapered surface 242 of the transitional stop 238 engages the proximal tapered surfaces 234a–234n of the stationary stop 230, a desired longitudinal relationship is dependably generated between the jet cap 240 and the catheter distal end 33a. Most importantly, the jet cap 240 is oriented and spaced apart and distally situated at a desired relationship to the distal end 33a of the catheter 32.

Figure 22:
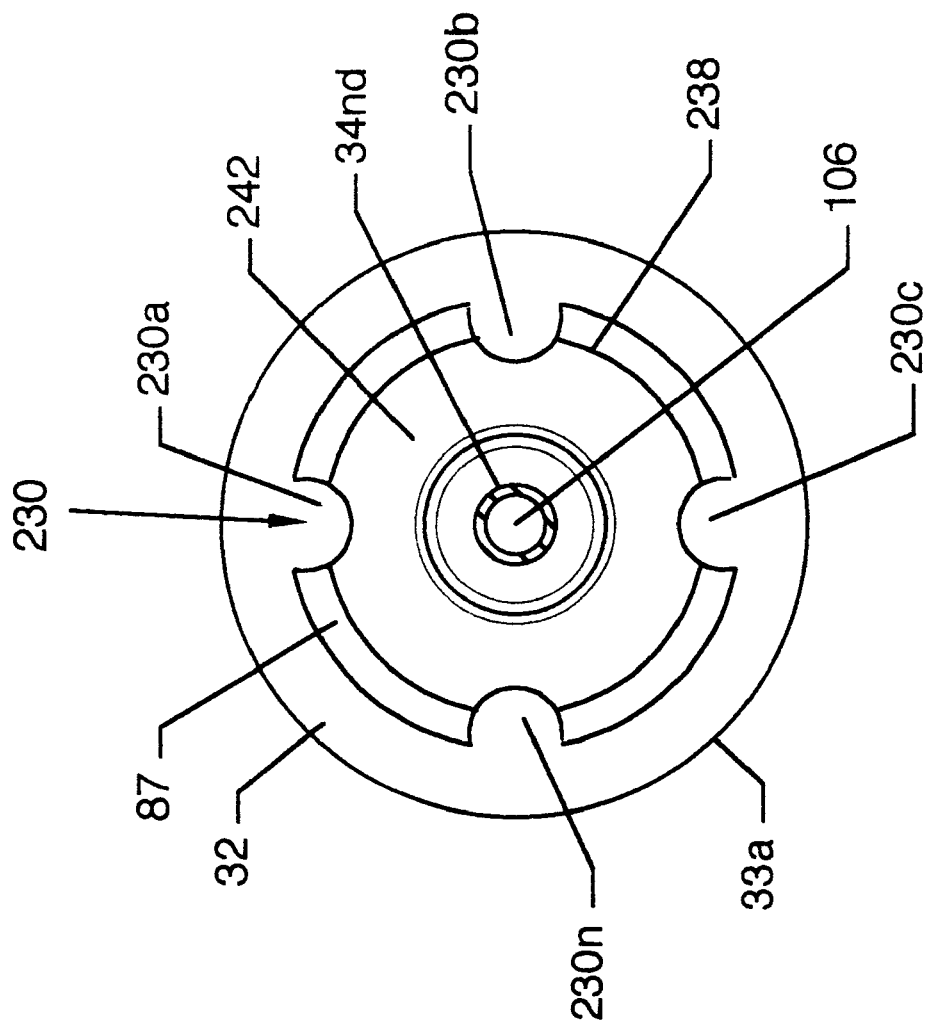
FIG. 22 is a view of the catheter distal end looking in the direction of line 22—22 of FIG. 21, with the hypo-tube shown in cross section.

FIG. 22 illustrates a view of the catheter distal end 33a looking in the direction of line 22—22 of FIG. 21, where all numerals correspond to those elements previously or otherwise described. Illustrated in particular are the plurality of arcuate stops 230a–230n shown in contact with the distal tapered surface 242 of the transitional stop 238. Fluids containing thrombotic debris can pass between the arcuate stops 230a–230n, along the inner wall of the catheter 32 which is adjacent to and between the arcuate stops 230a–230n, along the transitional stop 238, and into the lumen 87 of the catheter 32 for passage to the manifold 16.

Figure 23:
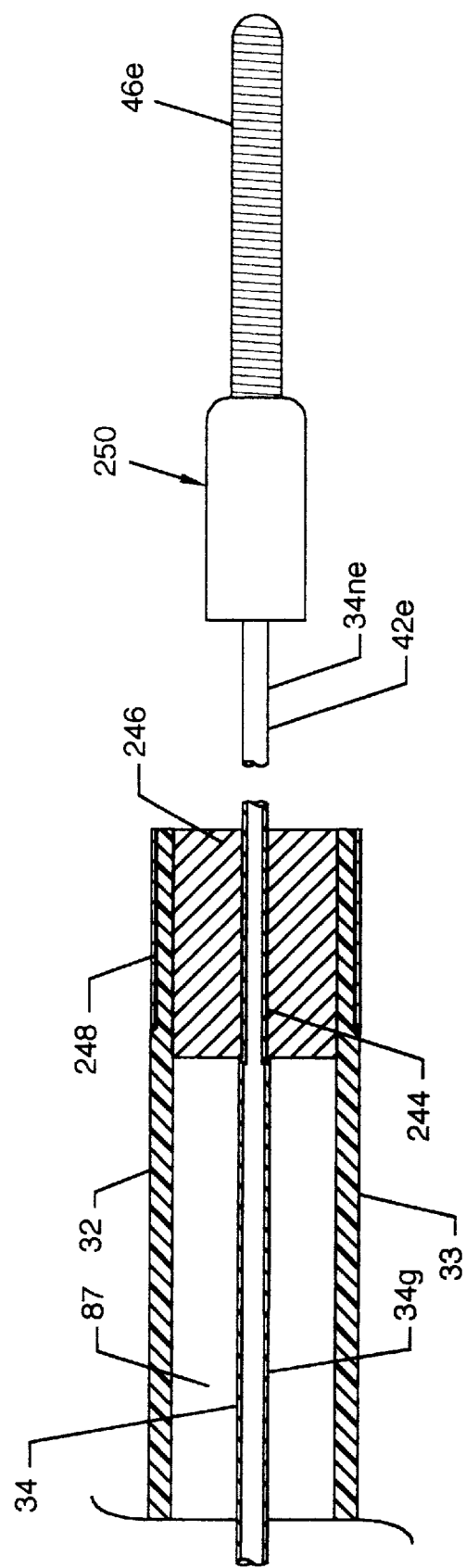
FIG. 23 is a side view in partial cross section of a fifth alternative embodiment of the catheter distal end, where the hypo-tube is fixed along the longitudinal axis of the catheter.

FIG. 23, a fifth alternative embodiment, illustrates, in partial cross section, a side view of the catheter distal end 33 where the hypo-tube 34 is fixed along the longitudinal axis of the catheter 32, where all numerals correspond to those elements previously or otherwise described. In this embodiment of a one-piece catheter, the hypo-tube 34 is appropriately aligned and secured in a central bore 244 of a cylindrical fixture 246 which secures in the end of the catheter 32 by a crimp sleeve 248. A jet cap 250 and a guidewire coil 46e secure to the hypo-tube distal end 42e at the last hypo-tube portion 34ne at a fixed distance from the catheter distal end 33. In this embodiment, no transitional or stationary stops are incorporated, as the entire catheter system incorporating a longitudinally fixed hypo-tube 34 is inserted into the body without use of a guidewire. The cylindrical fixture 246 has passages with the same profile as passages 162a–162n of the transitional stop 40 for connection to lumen 87 in the catheter 32.

Figure 24:
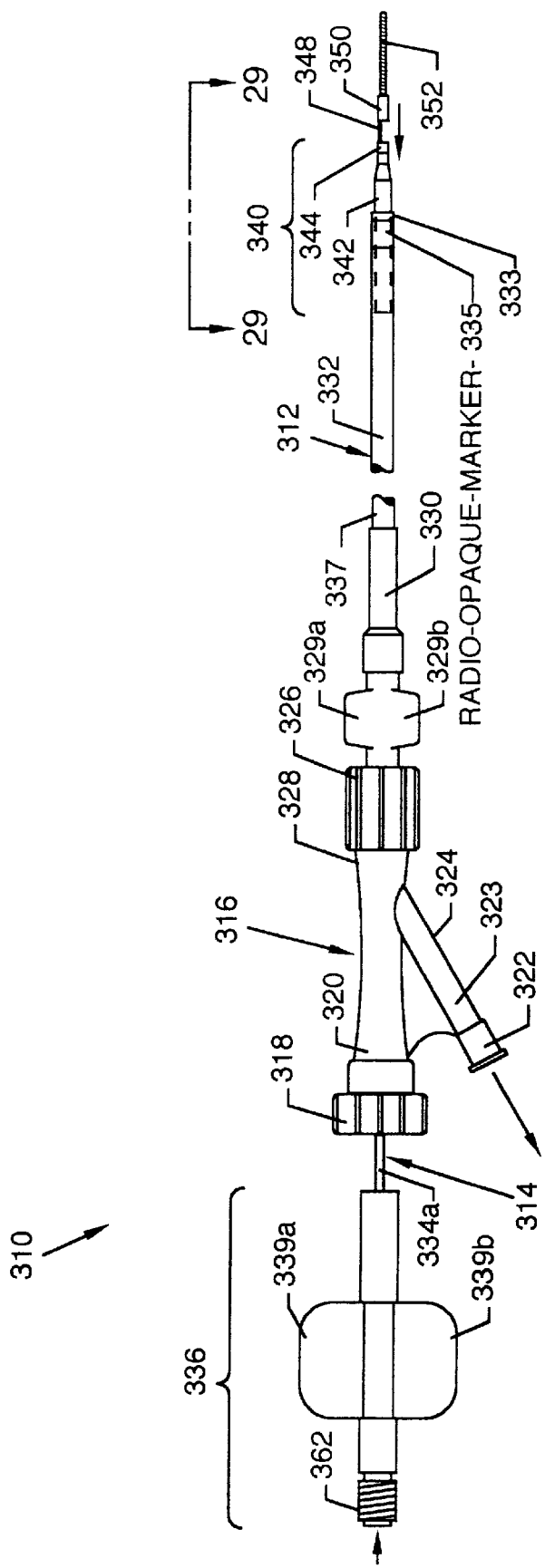
FIG. 24 is a side view of a sixth alternative embodiment of a rheolytic thrombectomy catheter.
Figure 25:
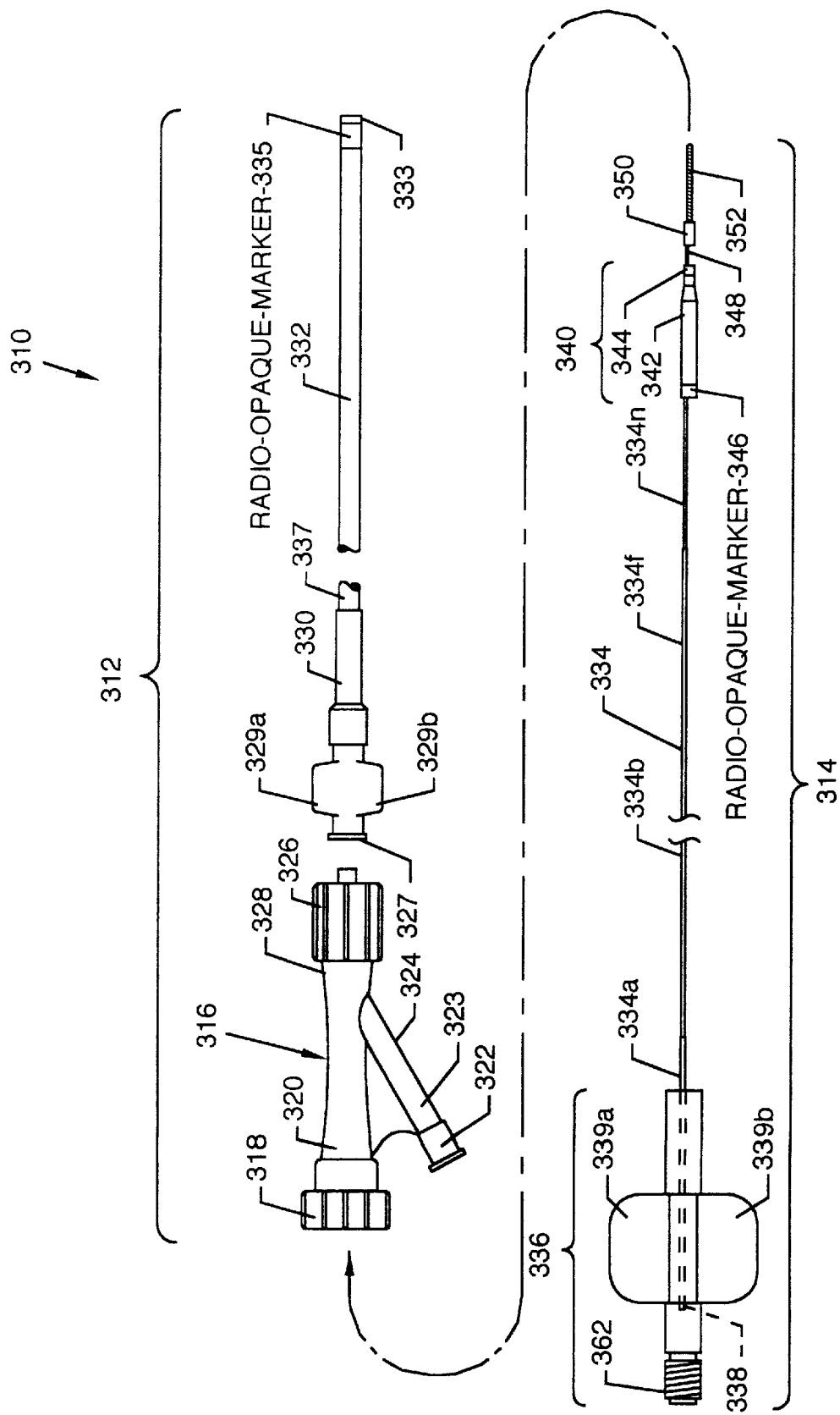
FIG. 25 is a semi-exploded side view of the rheolytic thrombectomy catheter of FIG. 24.

FIG. 24, a sixth alternative embodiment, illustrates a side view of a rheolytic thrombectomy catheter 310, useful for the removal of thrombus, and FIG. 25 illustrates a semi-exploded side view of the rheolytic thrombectomy catheter 310. The rheolytic thrombectomy catheter 310 includes two major assemblies: namely, an outer assembly 312 and an inner assembly 314 as best shown in FIG. 25. The majority of the components of the rheolytic thrombectomy catheter 310 are comprised of tubular members as described herein. The inner assembly 314 aligns concentrically to and within the outer assembly 312 and extends beyond the length of the outer assembly 312.

Figure 26:
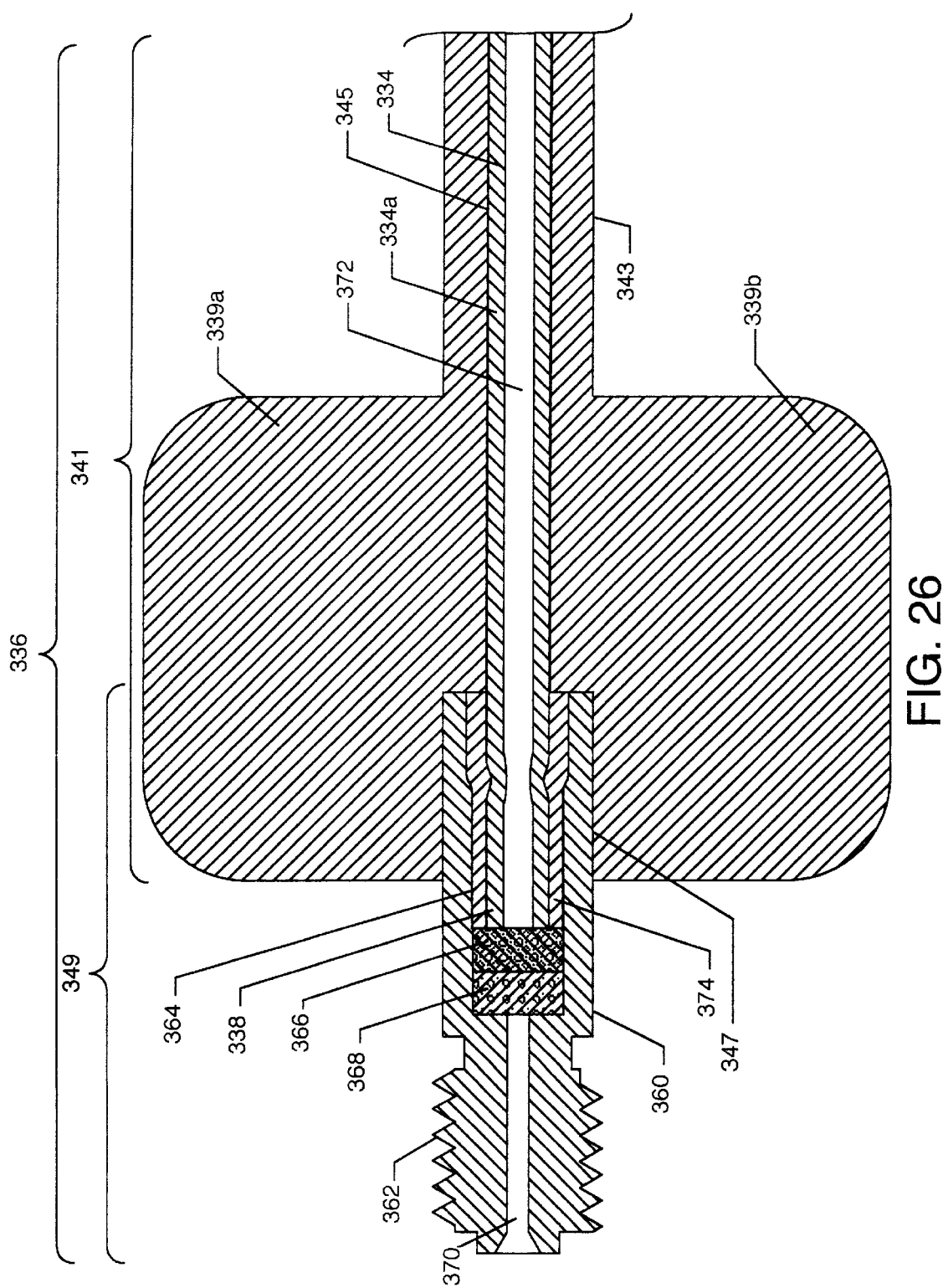
FIG. 26 is a longitudinal sectional view of the filter housing/high pressure connection/stop assembly located at the proximal end of the hypo-tube of the sixth alternative embodiment.

Externally visible components, or portions of components, of the outer assembly 312 of the rheolytic thrombectomy catheter 310, as illustrated in FIGS. 24 and 25, include a manifold 316, also known as a Y-adapter, a hemostasis nut/stop 318 secured to the proximal end 320 of the manifold 316, a Luer connection 322 located at the proximal end 323 of an angled manifold branch 324 extending from the manifold 316, a rotatable Luer fitting 326 (screw cap) secured to the distal end 328 of the manifold 316, a Luer connection 327 having a strain relief 330 and opposing manipulation tabs 329a and 329b which secures to the distal end 328 of the manifold 316 by the rotatable Luer fitting 326, and a first tube or catheter 332, having a distal end 333, secured at the catheter proximal end 337 to the manifold 316 by the strain relief 330 and rotatable Luer fitting 326 and the Luer connection 327. A radio-opaque marker 335 is positioned and fixed over and about the catheter distal end 333. The externally visible components of the inner assembly 314, illustrated in FIG. 25, include a high pressure second tube or hypo-tube 334, a filter housing/high pressure connection stop assembly 336, having opposing manipulation tabs 339a and 339b, which concentrically aligns to and secures over and about the proximal end 338 (FIG. 26) of the hypo-tube 334, a flow director 340 having and being comprised of a connecting expandable exhaust tube 342, a connecting inner body 344, and an optional radio-opaque marker 346 which passes over and about the hypo tube 334 near hypo-tube distal end 348, a jet cap 350 secured to the hypo-tube distal end 348, and a guidewire coil 352 concentrically aligned to and secured to one end of the jet cap 350. The high pressure hypo-tube 334 is drawn and is tapered in incremental steps to provide degrees of flexibility along its length. For purposes of example and illustration, the hypo-tube 334 can include a hypo-tube portion 334a at the hypo-tube proximal end 338 having an outer diameter of 0.018 inch or smaller, and can include a plurality of incrementally stepped down hypo-tube portions 334b–334n each of lesser outer diameter, where the last hypo-tube portion 334n is stepped down to an outer diameter range of 0.006 to 0.012 inches at the hypo-tube distal end 348. The hypo-tube 334 becomes increasingly more flexible from the hypo-tube proximal end 338 towards the hypo-tube distal end 348 due to the incremental diameter decrease along its length. Increasing flexibility along the length of the hypo-tube 334 allows for easier flexed penetration into tortuous vascular paths. Although the hypo-tube 334 is stepped down in increments, the hypo-tube 334 can also be fashioned of a constantly decreasing outer diameter to provide increasing flexibility along its length and shall not be construed to be limiting to the scope of the invention.

PIG. 26 illustrates a longitudinal sectional view of the filter housing/high pressure connection stop assembly 336 located at the proximal end 338 of the hypo-tube 334, where all numerals correspond to those elements previously or otherwise described. The proximally located filter housing/high pressure connection stop assembly 336 includes a filter housing 349 which mounts in a grasping assembly 341. The filter housing 349 has a cylindrical-like body 360 having a threaded surface 362 utilized for high pressure connection extending therefrom, a tubular cavity 364, fine and course filters 366 and 368 residing in the tubular cavity 364, a central passage 370 concentric to and co-located with the threaded surface 362 and extending through the proximal end of the body 360 and connecting to the tubular cavity 364, and a ferrule 374 residing in the tubular cavity 364 juxtaposing fine filter 366. The grasping assembly 341 includes a tubular body 343 terminating in manipulating tabs 339a and 339b and includes a central bore 345 extending through the tubular body 343 and partially into the region of the manipulating tabs 339a and 339b to intersect bore 347. Bore 347 in the grasping assembly 341 accommodates the body 360 of the filter housing 349 which is suitably secured thereto and therein. The hypo-tube proximal end 338 extends through bore 345 of the tubular body 343 and suitably secures within and frictionally engages the interior of the ferrule 374. The central passage 370 communicates through fine and course filters 366 and 368 with the lumen 372 of the hypo-tube 334.

Figure 27:
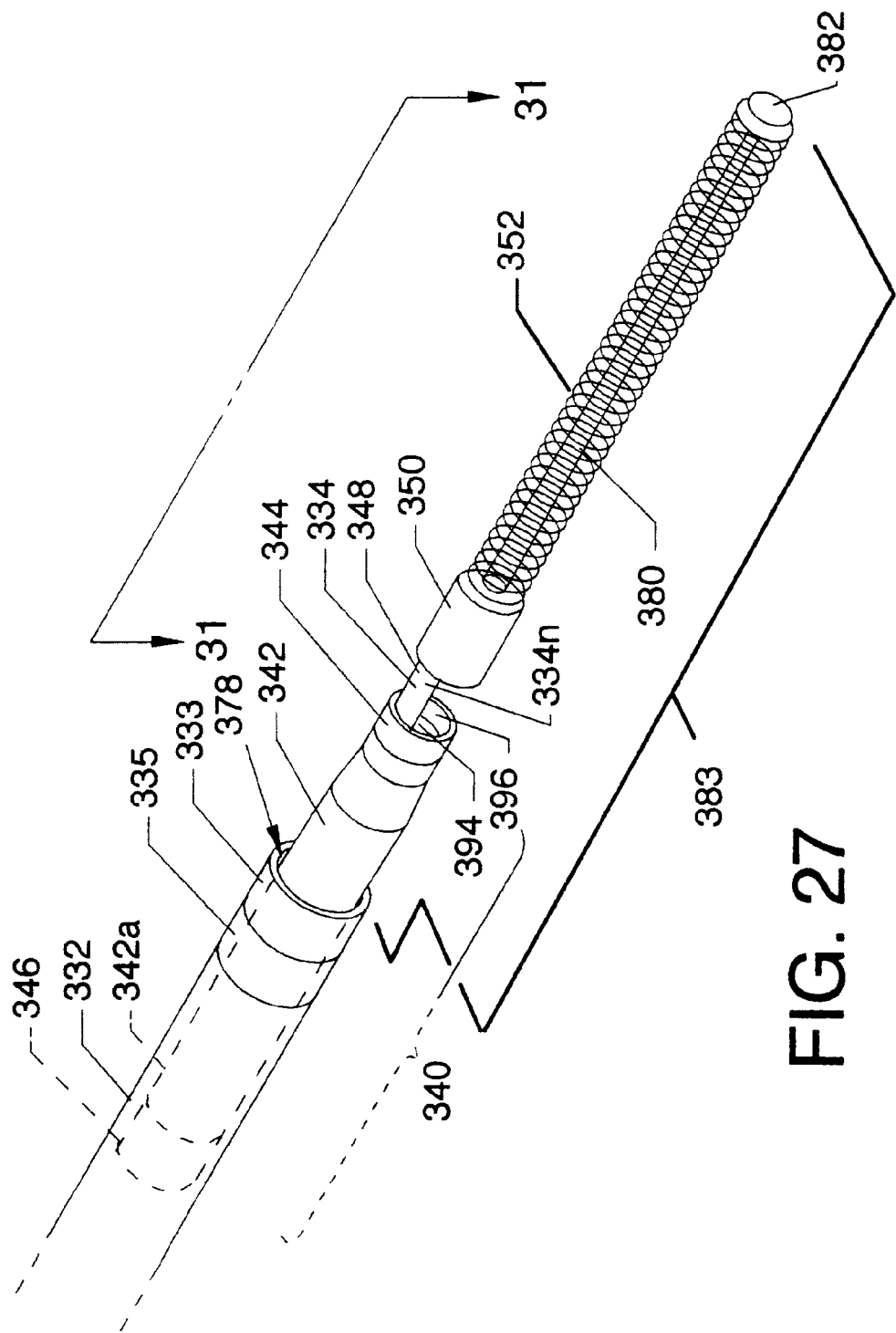
FIG. 27 is an isometric view of the flow director, the jet cap and the guidewire coil of the sixth alternative embodiment.
Figure 28:
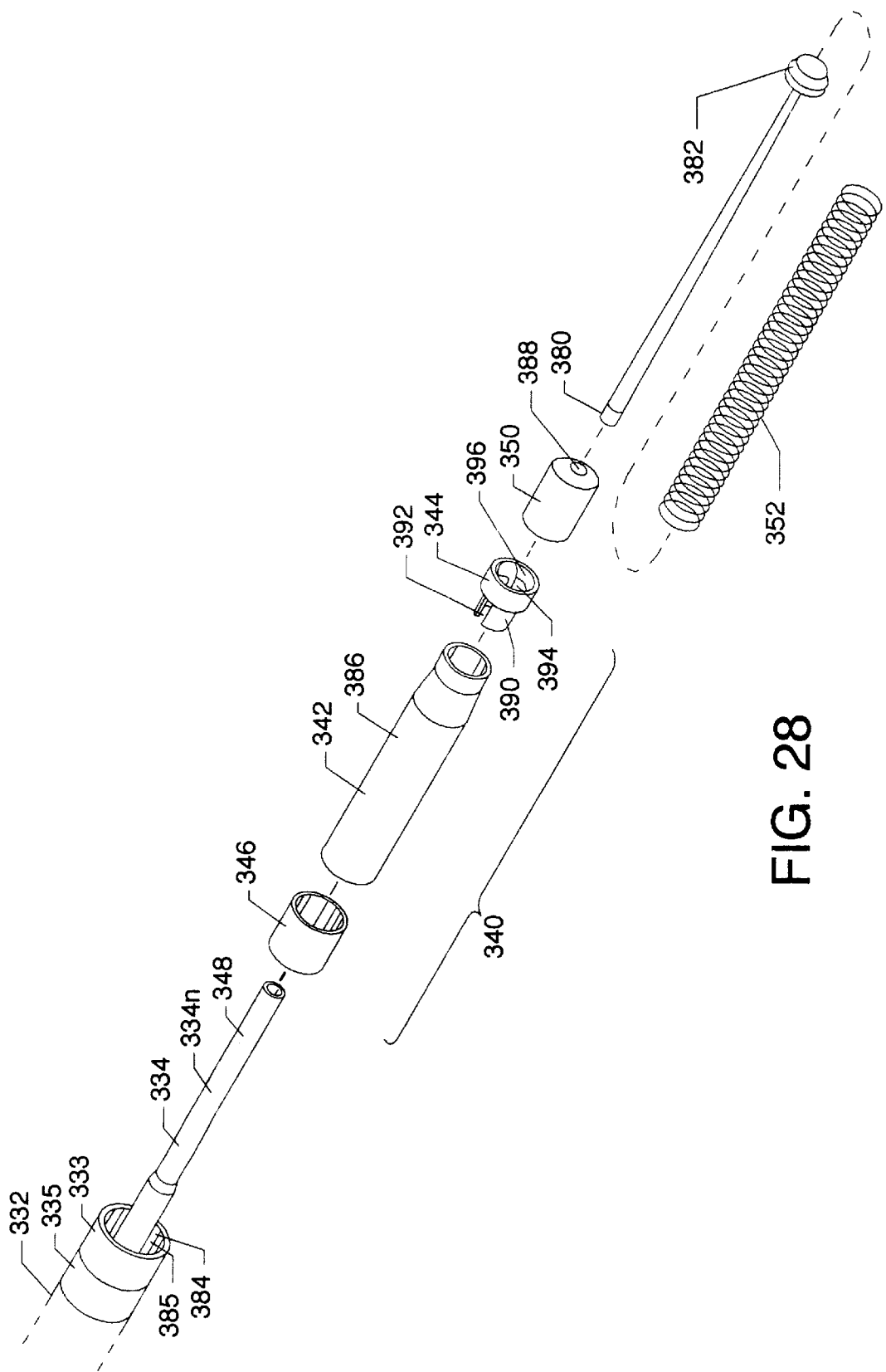
FIG. 28 is an exploded isometric view of the flow director, the jet cap, and the guidewire coil shown in FIG. 27.

FIG. 27 illustrates an isometric view of the flow director 340, the jet cap 350 and the guidewire coil 352, and FIG. 28 illustrates an exploded isometric view of the flow director 340, the jet cap 350 and the guidewire coil 352, where all numerals correspond to those elements previously or otherwise described. The hypo-tube 334 extends proximally through the flow director 340, and collectively the hypo-tube 334 and the flow director 340 extend proximally through the catheter 332. As illustrated in the unpressurized mode, it is noted that an annulus 378 is formed between the interior annular surface 384 of the catheter 332 and the outer annular surface 386 of the expandable exhaust tube 342. During normal pressurized operation, the expandable exhaust tube 342 expands to cause the outer annular surface 386 of the expandable exhaust tube 342 to expand and impinge the interior annular surface 384 of the catheter 332, thereby eliminating the annulus 378, as later described in detail. The guidewire coil 352 includes a centrally located tapered core 380 of decreasing taper distally to increase flexibility in a distal direction. A weld 382 is also included at the distal end of the guidewire coil 352 to secure the distal end of the tapered core 380 to the guidewire coil 352 distal end and to provide for smooth entry into a vessel or other body cavity. The proximal end of the tapered core 380 suitably secures to a bore 388 at one end of the jet cap 350. The proximal end of the guidewire coil 352 suitably secures to the jet cap 350. The inner body 344 includes a reduced radius neck 390 which is accommodated by the distal end of the expandable exhaust tube 342. The reduced radius neck 390 also includes a slotted cutout 392 for mounting, such as by welding or other suitable means, of the distal end 348 of the hypo-tube 334. Also included, in the interior of the inner body 344, is a passage 394 having a ramped annular surface 396.

As the hypo-tube 334 is positioned, during pressurized or unpressurized operation, the flow director 340, the jet cap 350, the guidewire coil 352, and tapered core 380, along with the hypo-tube 334, move and position as a unit to a desired position along a variable displacement distance 383 which is the distance from the distal end 333 of the catheter 332 to the weld 382 at the distal end of the guidewire coil 352. The variable displacement distance 383 can range from a minimum distance where the weld 382 at the distal end of the guidewire coil 352 is positioned just inside the distal end 333 of the catheter 332 to a distance where the proximal end 342a of the expandable exhaust tube 342 is positioned just inside the distal end 333 of the catheter 332, whereby a major portion of the expandable exhaust tube 342, the inner body 344, the space 406, the jet cap 350, the guidewire coil 352, and the tapered core 380 are distally located with reference to the distal end 333 of the catheter 332. At this extended position, further distal movement is prevented by impingement of the filter housing/high pressure connection/ stop assembly 336 with the hemostasis nut/stop 318 shown in FIG. 24.

Figure 29:
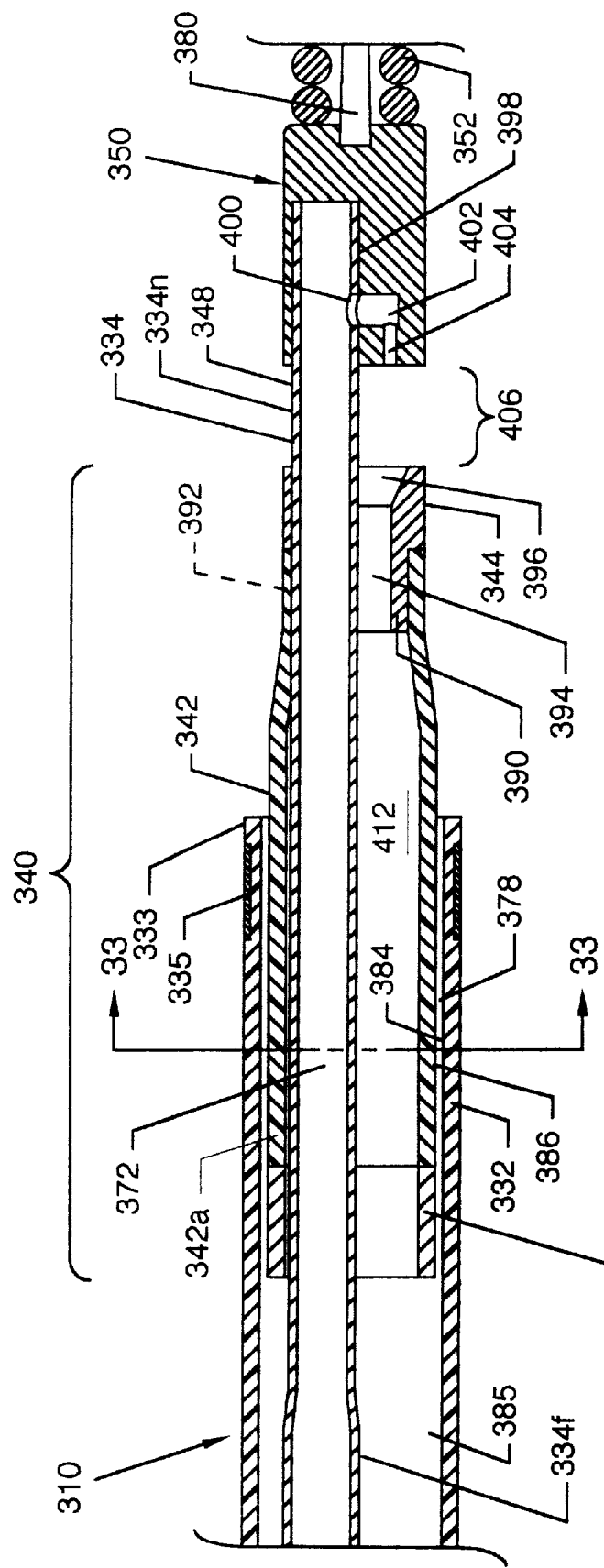
FIG. 29 is a view in cross section of the flow director, the jet cap and the guidewire coil along line 29—29 of FIG. 24 in the unpressurized mode.

FIG. 29 illustrates a view in cross section of the flow director 340, the jet cap 350 and the guidewire coil 352 along line 29—29 of FIG. 24 in the unpressurized mode, where all numerals correspond to those elements previously or otherwise described. Illustrated in particular is the relationship of the interior annular surface 384 of the catheter 332 and the outer annular surface 386 of the expandable exhaust tube 342 which form the annulus 378. Also illustrated is the jet cap 350 which secures over and about the distal end 348 of the hypo-tube 334. A horizontally aligned bore 398 in the upper region of the jet cap 350 accommodates the distal end 348 of the hypo-tube 334 which suitably secures and seals therein. An orifice 400 located in the distal end 348 of the hypo-tube 334 aligns with a vertically aligned passage 402 to further communicate with a horizontally aligned and rearwardly or proximally aimed jet 404. A predetermined and suitable space 406, is located between the proximal end of the jet 404, which is aligned with the proximal end of the jet cap 350, and, in general, the catheter distal end 333, and, more specifically, to distal end of the ramped annular surface 396 of the inner body 344. The maximum distal position of the space 406 with relation to the catheter distal end 333 is determined by the relationship of the distal end of the filter housing/high pressure connection stop assembly 336 (FIG. 24) and the hemostasis nut/ stop 318 which contact each other to limit the distal movement of the hypo-tube 334. The location of space 406 can be determined by observation of the relationship of one or more of the following components, including the radio-opaque marker 335 at the catheter distal end 333, the radio-opaque marker 346, the inner body 344, the jet cap 350, and most commonly by the guidewire coil 352 which is made of platinum, or other components by known observation methods. The hypo-tube 334 can be fashioned of material such as, but not limited to, stainless steel or nickel titanium alloys.

Figure 30:
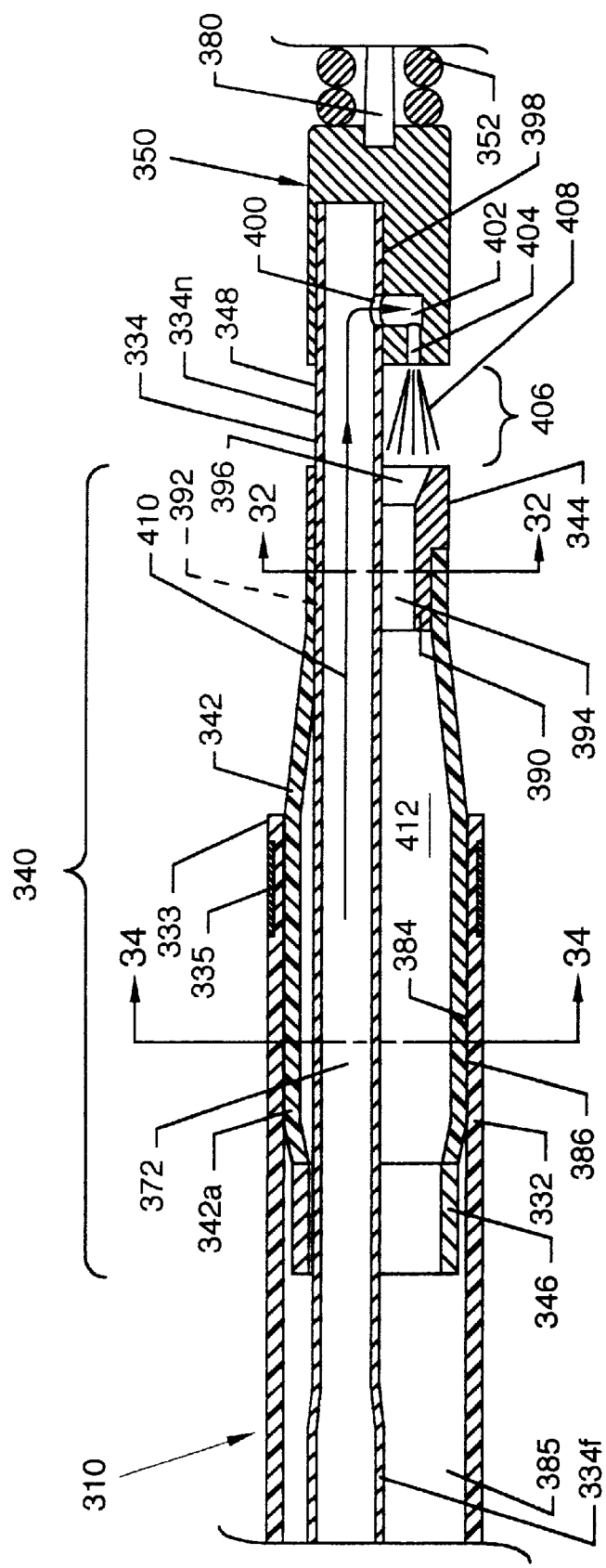
FIG. 30 is a view in cross section of the flow director, the jet cap and the guidewire coil along line 29—29 of FIG. 24 in the pressurized mode.
Figure 30A:
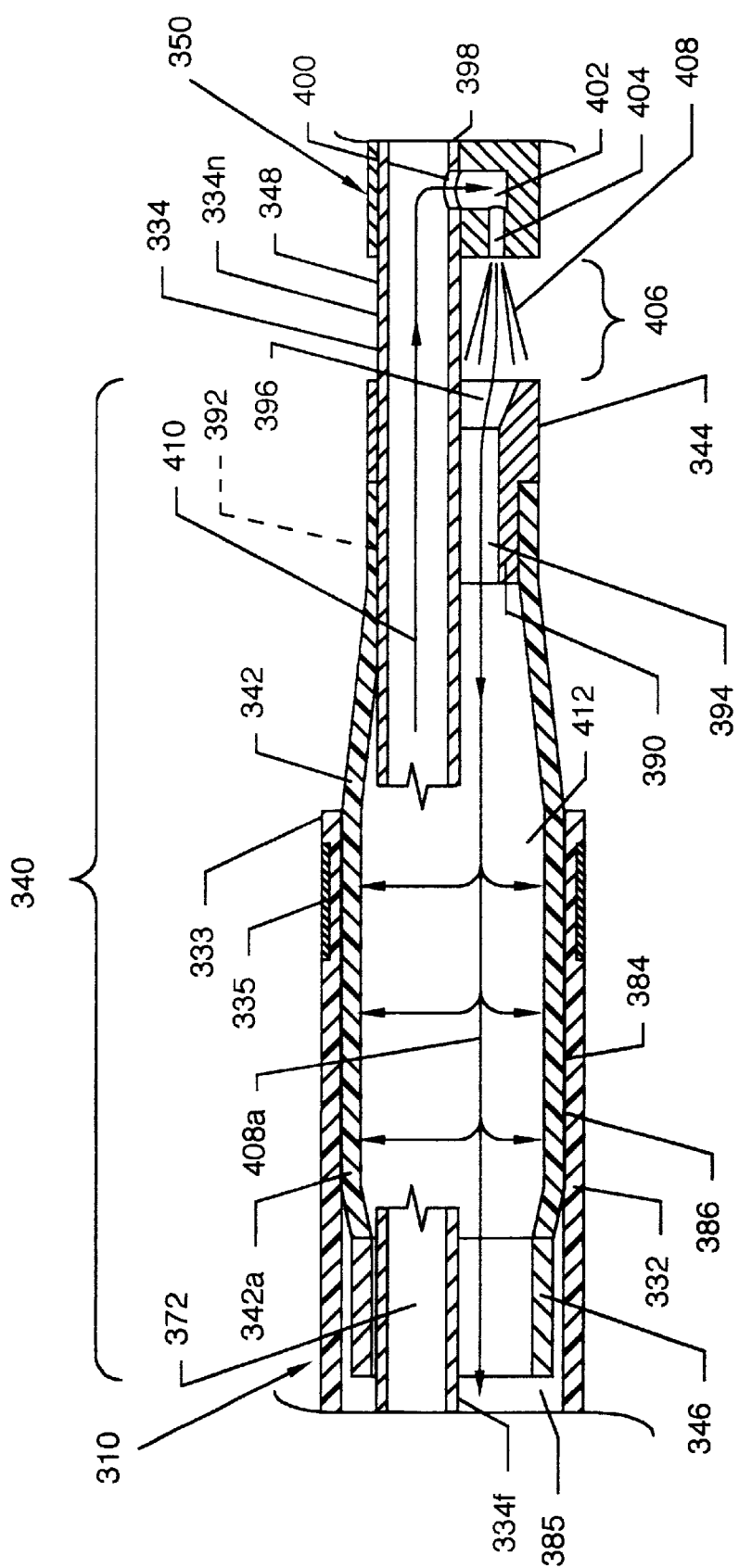
fig. 30A is an expanded portion of FIG. 30 detailing interaction of the saline jet flow on the expandable exhaust tube.

FIG. 30 illustrates a view in cross section of the flow director 340, the jet cap 350 and the guidewire coil 352 along line 29—29 of FIG. 24 in the pressurized mode, where all numerals correspond to those elements previously or otherwise described. Subsequent to proper positioning of the appropriate component of the invention in a vessel or other body member in the unpressurized mode, saline 410, under high pressure, is injected through the inner assembly 314 and through the hypo-tube 334 and delivered to the distal hypo-tube portion 334n, orifice 400, passage 402 and thence to jet 404 in the jet cap 350. The pressurized saline exits the jet 404 as a saline jet flow 408 and is directed partially into the ramped annular surface 396 and the passage 394 of the inner body 344 and into the lumen 412 of the expandable exhaust tube 342 to pressurize the expandable exhaust tube 342 causing the expandable exhaust tube 342 to expand and force the expandable exhaust tube outer annular surface 386 to seal against the catheter interior annular surface 384. This is depicted in FIG. 30A where saline jet flow 408a, continuing from saline jet flow 408, pressurizes expandable exhaust tube 342 and causes the exhaust tube 342 to expand. The saline jet flow 408 also flows to entrain thrombotic tissue adjacent to or lying within the space 406 to break up and erode the thrombotic tissue. Positive pressurized flow of the pressurized saline and the entrained particles of thrombotic tissue is prevented from back flowing out of the previously open annulus 378 which has been subsequently closed by the seal between the inner assembly 314 within the outer assembly 312 and is allowed to travel under full pressurized force along the lumen 412 of the expandable exhaust tube 342 and along a catheter lumen 385 to the manifold 316 and outwardly through the angled manifold branch 324. The ability to insert and maneuver the inner assembly 314 within the outer assembly 312 freely and unhampered and then to subsequently effect a seal between the inner assembly 314 and the outer assembly 312 while maintaining maneuverability contributes to the novelty and usefulness of the invention.

FIG. 31 illustrates a view in cross section of the jet cap 350 and the guidewire coil 352 along line 31—31 of FIG.

27, where all numerals correspond to those elements previously or otherwise described.

FIG. 32 illustrates a view in cross section of the junction of the inner body 344 and the expandable exhaust tube 342 along line 32—32 of FIG. 30, where all numerals correspond to those elements previously or otherwise described. Illustrated in particular is the mounting and the securing of the hypo-tube 334 to opposing sides of the slotted cutout 392 in the reduced radius neck 390 of the inner body 344 by welds 414 and 416. Positioning and securing of the hypo-tube 334 in the upper region of the inner body 344 ensures alignment of the jet cap 350, and thus the jet 404, with the inner body 344.

Figure 33:
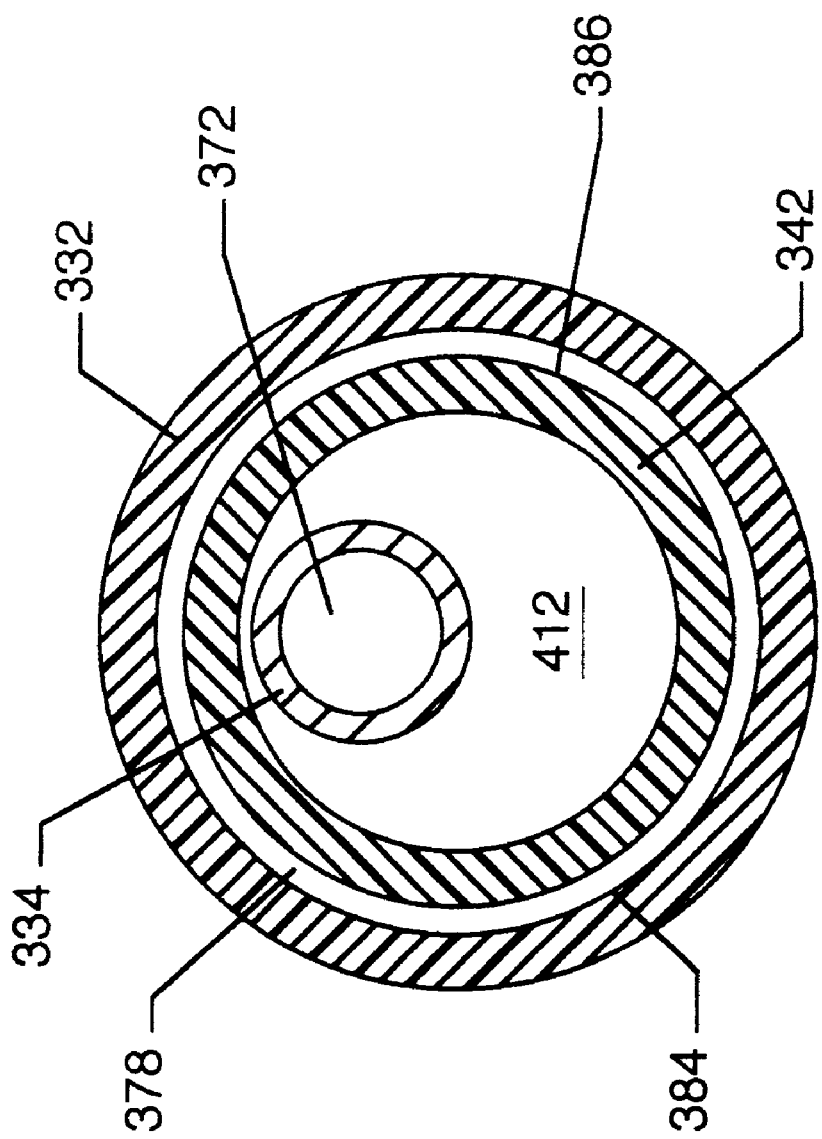
FIG. 33 is a view in cross section of the distal end of the rheolytic thrombectomy catheter along line 33—33 of FIG. 29 in the unpressurized mode.

FIG. 33 illustrates a view in cross section of the distal end of the rheolytic thrombectomy catheter 310 along line 33—33 of FIG. 29 in the unpressurized mode, where all numerals correspond to those elements previously or otherwise described. Illustrated in particular is the annulus 378 between the catheter interior annular surface 384 and the expandable exhaust tube outer annular surface 386. Annulus 378 allows for ready and adequate passage of the flow director 340 through the catheter 332 during positioning of the inner assembly 314 (FIG. 25).

Figure 34:
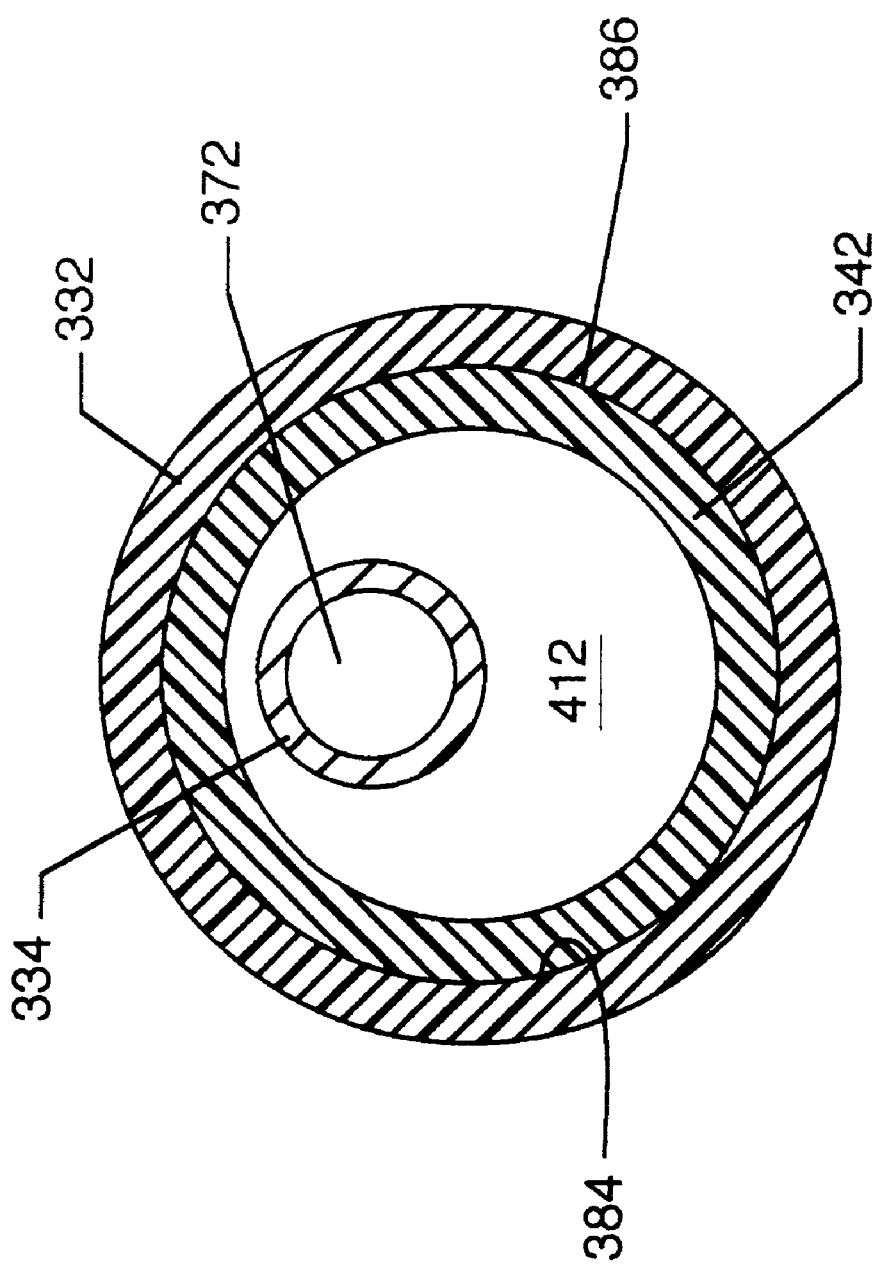
FIG. 34 is a view in cross section of the distal end of the rheolytic thrombectomy catheter along line 34—34 of FIG. 30 in the pressurized mode; and, FIG. 35 is a view in cross section and in partial cutaway of the distal end of the rheolytic thrombectomy catheter of FIG. 24 in operation in a blood vessel.

FIG. 34 illustrates a view in cross section of the junction of the distal end of the rheolytic thrombectomy catheter 310 along line 34—34 of FIG. 30 in the pressurized mode, where all numerals correspond to those elements previously or otherwise described. Illustrated in particular is the closing or elimination of the annulus 378 (FIG. 33) between the catheter interior annular surface 384 and the expandable exhaust tube outer annular surface 386. Closing of the annulus 378 allows for sealing of the flow director 340 against the catheter interior annular surface 384 to maintain full pressurization (FIG. 25).

MODE OF OPERATION

Figure 35:
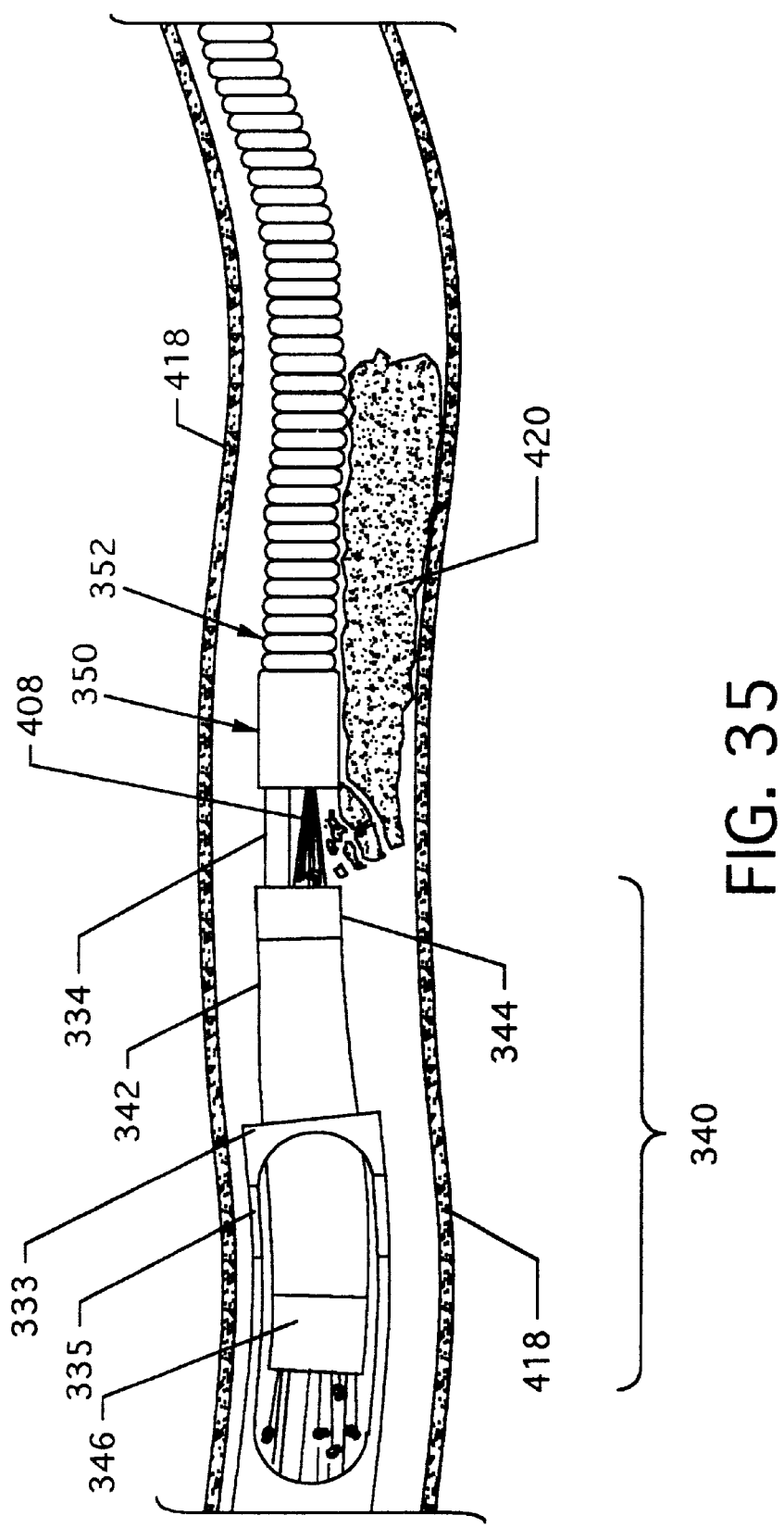

FIG. 35 illustrates a view in cross section and in partial cutaway of the distal end of the rheolytic thrombectomy catheter 310 in operation in a blood vessel 418. FIG. 35, with reference to elements previously or otherwise described in relation to FIGS. 24–34, best illustrates the mode of operation of the rheolytic thrombectomy catheter 310, with particular attention to the catheter distal end 333, the flow director 340 and the jet cap 350 positioned in a blood vessel 418, artery or the like at the site of a thrombotic deposit and lesion 420.

A removable 13 of FIG. 2 guidewire is first advanced percutaneously through the vasculature to the site of the thrombotic deposit and lesion 420. For a distal coronary vessel or a vessel of the brain, typically the guidewire 13 has a diameter which can range from 0.010–0.016 inches. This invention can also be applied to larger vessels which require larger diameter guidewires. Once a guidewire 13 has been advanced along the vessel 418 and has reached the thrombotic deposit and lesion 420, catheter 332, the first tube, which serves as a flexible evacuation tube, can be advanced over the guidewire through tortuous turns to reach the thrombotic deposit and lesion 420. With the catheter distal end 333 of the catheter 332 positioned near the thrombotic deposit and lesion 420, the guidewire 13 can then be removed from the catheter 332 and the patient's body. The jet cap 350, which can have a lubricious coating to aid in deployment through the lumen 385 of the catheter 332, and guidewire coil 352, at the terminus of the second tube or hypo-tube 334, is then advanced within the lumen 385 of the catheter 332 to a position along the variable deployment distance 383 where the tapered core 380, the guidewire coil 352, the space 406, the inner body 344, and the expandable exhaust tube 342 are positioned as desired beyond the distal end 333 of the catheter 332, whereby the expandable exhaust tube 342 is aligned to the distal end 333 of the catheter 332. The hypo-tube 334 can be of stainless steel or nickel titanium alloy. The passage 394 of the inner body 344, the lumen 412 of the expandable exhaust tube 342, and the lumen 385 of the catheter 332 serve as an evacuation tube at the catheter distal end 333. The rheolytic thrombectomy catheter 310 can then be activated by providing high pressure liquid, preferably saline, to the proximal end of the catheter 332 via the manifold 316.

High pressure saline 410, or other liquid, from the manifold 316 is provided and flows through the lumen 372 of the hypo-tube 334 to enter orifice 400 and passage 402 leading to the jet 404 of the jet cap 350 (FIG. 30). The high pressure saline exits jet 404 as high velocity saline jet flow 408 being directed toward the open ramped annular surface 396 in the inner body 344 at the catheter distal end 333:

(1) to close the annulus 378 to ensure positive flow without leak-back through an annulus such as annulus 378, as previously described; and, (2) to dislodge tissue from the thrombotic deposit and lesion 420 and entrain the tissue into the saline jet flow 408 where it is broken up into smaller fragments and carried proximally.

Impingement of the saline jet flow 408 into the flow director 340 and the co-located catheter distal end 333 opening creates a stagnation pressure within the flow director lumen 412 and catheter lumen 385 (evacuation lumen) that drives the debris particles of thrombotic deposit tissue and lesion 420 toward the proximal end of the catheter 332.

A positive displacement piston pump (not illustrated) can be used to provide liquid, preferably saline, under pressure to the proximal end of the hypo-tube 334. A pressure ranging from 500–15,000 psi will provide the energy to create a useful high velocity saline jet flow 408 as the saline exits the jet 404 located at the proximal surface of the jet cap 350. The flow rate of saline can be controlled by adjusting the pumping rate of the positive displacement piston pump. The proximal end of the catheter 332 interfaces with a metering device through the Luer connection 327 at the manifold branch 324, for example, a roller pump, prior to discharge of the evacuated thrombotic debris into a collection bag for disposal. The rate of evacuation can be controlled by adjusting the rate of the roller pump. The rate of saline inflow can be balanced with the rate of removal of thrombotic debris by simultaneous adjustment of the piston pump and the roller pump. The rate of saline inflow can be less than, equal to, or greater than the rate of removal of thrombotic debris. The rate of thrombus removal can be set to slightly exceed the rate of saline inflow to reduce the likelihood for distal embolization of thrombotic tissue.

Because numerous modifications may be made to this invention without departing from the spirit thereof, the scope of the invention is not to be limited to the embodiments illustrated and described. Rather, the scope of the invention is to be determined by the appended claims and their equivalents. The tip at weld 382 can be radio-opaque. The guidewire, coil and mandrel can also be radio-opaque material, such as platinum, iridium or gold alloy. Alternatively, the guidewire coil 352 can be a braided polymer or other suitable material, such as a platinum coil. The guidewire core can be tapered to provide a gradual transition from flexible to stiff in order to negotiate the neuroanatomy. The length can be 0.2 to 2 cm. The exhaust tube portion can direct flow into the exhaust tube and when pressurized can expand to provide a seal.

Various modifications can be made to the present invention without departing from the apparent scope hereof.

RHEOLYTIC THROMBECTOMY CATHETER AND METHOD OF USING SAME

PARTS LIST

| | |
|---|---|
| 10 | rheolytic thrombectomy catheter |
| 12 | outer assembly |
| 14 | inner assembly |
| 16 | manifold |
| 18 | hemostasis nut |
| 20 | manifold proximal end |
| 22 | Luer connection |
| 23 | proximal end (branch) |
| 24 | branch |
| 26 | Luer fitting |
| 28 | distal manifold end |
| 30 | strain relief |
| 31 | tube |
| 32 | first tube or catheter |
| 33 | catheter distal end |
| 33a | catheter distal end |
| 34 | second tube or hypo-tube |
| 34a–n | hypo-tube portions |
| 34n | last hypo-tube portion |
| 34na | last hypo-tube portion |
| 34nb | last hypo-tube portion |
| 34nc | last hypo-tube portion |
| 34nd | last hypo-tube portion |
| 34ne | last hypo-tube portion |
| 34x | U-shaped hypo-tube portion |
| 36 | filter housing/high pressure connection assembly |
| 38 | hypo-tube proximal end |
| 40 | transitional stop |
| 42 | hypo-tube distal end |
| 42a | hypo-tube distal end |
| 42b | hypo-tube distal end |
| 42c | hypo-tube distal end |
| 42d | hypo-tube distal end |
| 42e | hypo-tube distal end |
| 44 | jet cap |
| 46 | guidewire coil |
| 46a | guidewire coil |
| 46b | guidewire coil |
| 46c | guidewire coil |
| 46d | guidewire coil |
| 46e | guidewire coil |
| 48 | central passage |
| 50 | branch passage |
| 52 | multi-radius cavity |
| 54 | round outer cavity portion |
| 56 | round inner cavity portion |
| 58 | threaded surface |
| 60 | seal |
| 61 | distal annular surface |
| 62 | body |
| 63 | annular surface |
| 64 | grasping surface |
| 66 | threaded surface |
| 68 | passageway |
| 72 | filter |
| 74 | central bore |
| 76 | annular flange |
| 78 | tapered proximal tube mouth end |

-continued

| | |
|---|---|
| 80 | distal tube end |
| 82 | tapered tube surface |
| 84 | threads |
| 86 | threads |
| 87 | lumen (of 32) |
| 88 | tapered central passage surface |
| 90 | body |
| 92 | threaded surface |
| 94 | tubular cavity |
| 96 | fine filter |
| 98 | course filter |
| 100 | central passage |
| 102 | cap |
| 104 | central bore |
| 106 | lumen (of 34) |
| 108 | body |
| 110 | central bore |
| 112a–n | guide bars |
| 114a–n | angled leading edges |
| 116a–n | arced surfaces |
| 117 | shoulder-like transition |
| 118 | peripheral wall |
| 118a | peripheral wall |
| 118b | peripheral wall |
| 120 | circular end wall |
| 120a | circular end wall |
| 120b | circular end wall |
| 122 | elongated hole |
| 124 | arcuate portion |
| 126 | arcuate portion |
| 128 | jet orifice |
| 130 | jet orifice |
| 132 | weld |
| 132a | weld |
| 132b | weld |
| 134 | tapered core |
| 134a | tapered core |
| 136 | orifice |
| 138 | orifice |
| 140 | central cavity |
| 140a | central cavity |
| 140b | central cavity |
| 142 | weld |
| 142a | weld |
| 142b | weld |
| 144 | jet orifice |
| 146 | jet orifice |
| 148 | bore |
| 150 | stationary stop |
| 152 | cylindrical body |
| 153 | cap |
| 154 | central bore |
| 156 | shoulder |
| 158 | angled annular surface |
| 160 | crimp sleeve |
| 162a–n | passages |
| 164 | blood vessel |
| 166 | thrombotic deposit and lesion |
| 170 | saline jet |
| 180 | jet cap |
| 182 | hole |
| 184 | hole |
| 200 | jet cap |
| 202 | hole |
| 206 | jet orifice |
| 210 | transitional stop |
| 212 | jet cap |
| 214 | angled annular surface |
| 216 | hole |
| 218 | lumen |
| 230 | stationary stop |
| 230a–n | arcuate stops |
| 234a–n | proximal tapered surfaces |

-continued

| | |
|---|---|
| 236a–n | distal tapered surfaces |
| 238 | transitional stop |
| 240 | jet cap |
| 242 | distal tapered surface |
| 244 | central bore |
| 246 | cylindrical fixture |
| 248 | crimp sleeve |
| 250 | jet cap |
| 310 | rheolytic thrombectomy catheter |
| 312 | outer assembly |
| 314 | inner assembly |
| 316 | manifold |
| 318 | hemostasis nut/stop |
| 320 | manifold proximal end |
| 322 | Luer connection |
| 323 | proximal end (branch) |
| 324 | branch |
| 326 | rotatable Luer fitting (screw cap) |
| 327 | luer connection |
| 328 | distal end (manifold) |
| 329a–b | manipulation tabs |
| 330 | strain relief |
| 332 | first tube or catheter |
| 333 | distal end (catheter) |
| 334 | second tube or hypo-tube |
| 334a–n | hypo-tube portions |
| 335 | radio-opaque marker |
| 336 | filter housing/high pressure connection/stop assembly |
| 337 | proximal end (catheter) |
| 338 | hypo-tube proximal end |
| 339a–b | manipulation tabs |
| 340 | flow director |
| 341 | grasping assembly |
| 342 | expandable exhaust tube |
| 343 | tubular body |
| 344 | inner body |
| 345 | central bore |
| 346 | radio-opaque marker |
| 347 | bore |
| 348 | distal end (hypo-tube) |
| 349 | filter housing |
| 350 | jet cap |
| 352 | guidewire coil |
| 360 | body |
| 362 | threaded surface |
| 364 | tubular cavity |
| 366 | fine filter |
| 368 | course filter |
| 370 | central passage |
| 372 | lumen |
| 374 | ferrule |
| 378 | annulus |
| 380 | tapered core |
| 382 | weld |
| 384 | interior annular surface of catheter |
| 385 | catheter lumen |
| 386 | outer annular surface of expandable exhaust tube |
| 388 | bore |
| 390 | reduced radius neck |
| 392 | slotted cutout |
| 394 | passage |
| 396 | ramped annular surface |
| 398 | bore |
| 400 | orifice |
| 402 | passage |
| 404 | jet |
| 406 | space |
| 408 | saline jet flow |
| 410 | saline |
| 412 | lumen |
| 414 | weld |
| 416 | weld |
| 418 | blood vessel |
| 420 | thrombotic deposit and lesion |

What is claimed is:

1. A rheolytic thrombectomy catheter for the removal of thrombus from a body vessel, said rheolytic thrombectomy catheter comprising:
   a. an evacuation tube containing a longitudinally positionable high pressure hypo-tube and flow director with a jet cap at the distal end thereof directing a solution backwards towards the distal end of said evacuation tube;
   b. an exhaust tube portion, affixed to said longitudinally positionable high pressure hypo-tube; and,
   c. said exhaust tube portion permitting rotational and longitudinal movement of said hypo-tube relative to said evacuation tube.

2. A rheolytic thrombectomy catheter for the removal of thrombus from a body vessel, said rheolytic thrombectomy catheter comprising:
   a. an evacuation tube containing a longitudinally positionable high pressure hypo-tube with a jet cap at the distal end thereof directing a solution backwards towards the distal end of said evacuation tube;
   b. an expandable exhaust tube portion, affixed to said hypo-tube;
   c. said expandable exhaust tube portion permitting rotational and longitudinal movement of said hypo-tube relative to said evacuation tube when in the relaxed, unexpanded state and engaging said evacuation tube to seal said hypo-tube in engagement with said exhaust tube when in the expanded state, while still providing movement relative to each other; and,
   d. means for causing said expandable exhaust tube to expand and engage said evacuation tube.

3. The catheter of claim 2, wherein jet pressure expands said expandable exhaust tube.

4. The catheter of claim 2, wherein said means for causing said expandable exhaust tube to expand comprises an aperture at a distal end portion of said expandable exhaust tube for receiving fluid emitted from said jet cap.

5. The catheter of claim 4, wherein said jet cap contains a rearwardly facing orifice opposite said aperture for directing a flow of said high pressure fluid into said expandable exhaust tube.

6. The catheter of claim 2, further including flexible guidewire means affixed to, and extending outwardly from, in axial alignment with the distal end of said jet cap.

7. The catheter of claim 6, wherein said flexible guidewire means comprises a coil spring and a tapered core.

8. The catheter of claim 7, wherein said tapered core is of a thickness of about 0.010 inches to 0.004 inches on proximal end to 0.004 inches to 0.002 inches on distal end.

9. The catheter of claim 2, wherein said hypo-tube carries said solution at an infusion pressure in a range of 500 to 15,000 psi.

10. A rheolytic thrombectomy catheter for removing material from a body cavity, the rheolytic thrombectomy catheter comprising:

a. an outer assembly including a proximally located manifold, a distally extending evacuation catheter, and means to manipulate the evacuation catheter interposed between the manifold and the evacuation catheter; and, b. an inner assembly including a hypo-tube catheter, the hypo-tube catheter having a distally located Jet cap means to form a proximally directed jet from a high pressure flow of liquid from the hypo-tube catheter, and a flow director, adjacent to but proximally spaced apart a desired distance from the jet cap to receive at least a portion of the proximally directed jet, means of providing a flow of high pressure liquid to the hypo-tube catheter, the hypo-tube catheter being movable within the outer assembly when high pressure liquid is not flowing into the hypo-tube catheter, means to manipulate the hypo-tube catheter proximally coupled to the hypo-tube catheter, and means to limit maximum distal movement of the inner assembly relative to the outer assembly coupled to the hypo-tube catheter.

11. The rheolytic thrombectomy catheter of claim 10, wherein the flow director includes an expandable exhaust tube, said expandable exhaust tube having a proximal aperture, a distal aperture, and a passage therebetween and the distal aperture includes a ramped annular surface.

12. The rheolytic thrombectomy catheter of claim 11, wherein the ramped annular surface tapers inwardly proximally.

13. The rheolytic thrombectomy catheter of claim 11, wherein the expandable exhaust tube further includes a distally located radio-opaque marker.

14. The rheolytic thrombectomy catheter of claim 10, wherein the hypo-tube catheter further includes a distally located radio-opaque marker.

15. The rheolytic thrombectomy catheter of claim 10, wherein the hypo-tube catheter further includes a distally located guidewire coil.

16. The rheolytic thrombectomy catheter of claim 10, wherein the inner assembly is separable from the outer assembly and insertable into the outer assembly.

17. The rheolytic thrombectomy catheter of claim 10, wherein the flow director includes a longitudinally oriented expandable exhaust tube, movable within the evacuation catheter in the absence of a jet from the jet cap and temporarily expandedly sealed within the evacuation catheter in response to the presence of a jet from the jet cap.

18. The rheolytic thrombectomy catheter of claim 10, wherein impingement of the jet on the evacuation lumen creates sufficient stagnation pressure to allow evacuation of debris with no need for additional suction on the proximal end of the evacuation lumen.

19. A rheolytic thrombectomy catheter for the removal of thrombus from a body vessel, the rheolytic thrombectomy catheter comprising:

a. an evacuation tube containing a longitudinally positionable high pressure hypo-tube with a jet cap at the distal end thereof directing a solution backwards towards the distal end of said evacuation tubes b. a flow director carried by the longitudinally positionable high pressure hypo-tube, the flow director located adjacent to but spaced apart from the jet cap by a predetermined distance;

c. the flow director having an expandable exhaust tube, the expandable exhaust tube having a lumen in fluid communication with the fluid directed backwards from the jet cap and expandable in response to high pressure associated with the fluid directed backward from the jet cap such that expandable exhaust tube expands to seal against the inner surface of the evacuation tube by closing an annulus defined between the inner surface of the evacuation tube and the outer surface of the expandable exhaust tube; and, d. wherein the pressurized flow director temporarily limits longitudinal movement of said hypo-tube relative to the evacuation tube and prevents leakback at the annulus.

20. The rheolytic thrombectomy catheter of claim 19, wherein the hypo-tube passes through the flow director.

21. The rheolytic thrombectomy catheter of claim 19, wherein said flow director includes a distal ramped annular surface.

22. The rheolytic thrombectomy catheter of claim 21, wherein the ramped annular surface tapers inwardly proximally.

23. The rheolytic thrombectomy catheter of claim 19, further including flexible guidewire means affixed to, and extending outwardly from, in axial alignment with the distal end of said jet cap.

24. The catheter of claim 23, wherein said guidewire is short and tapered, whereby said short tapered guidewire means is usable for directing and positioning the catheter in the vasculature.

25. A rheolytic thrombectomy catheter for the removal of thrombus from a body vessel, the rheolytic thrombectomy catheter comprising:

a. an evacuation tube containing a longitudinally positionable high pressure hypo-tube with a jet cap at the distal end thereof directing a solution backwards towards the distal end of said evacuation tube;

b. an exhaust tube portion, affixed to said hypo-tube, adjacent to but spaced apart from said jet cap; and, c. said exhaust tube portion permitting rotational and longitudinal movement of said hypo-tube relative to said evacuation tube.

26. The rheolytic thrombectomy catheter of claim 25, wherein the exhaust tube portion has an inner surface and an outer surface and the hypo-tube is affixed to the inner surface of the exhaust tube portion.

27. The rheolytic thrombectomy catheter of claim 25, wherein the exhaust tube portion has an inner surface and an outer surface and the exhaust tube portion expands in response to pressure against the inner surface to engage the evacuation tube and prevent movement relative to said evacuation tube.

28. The rheolytic thrombectomy catheter of claim 25, wherein the exhaust tube portion has an inner surface and an outer surface and the exhaust tube portion expands in response to pressure against the inner surface to seal the outer surface against the evacuation tube.

29. A rheolytic thrombectomy catheter for the removal of thrombus from a body vessel, the rheolytic thrombectomy catheter comprising:

a. an evacuation tube containing a longitudinally positionable high pressure hypo-tube with a jet cap at the distal end thereof directing a solution backwards towards the distal end of said evacuation tube;

b. an expandable exhaust tube portion, affixed to said hypo-tube adjacent to, yet spaced apart from, said jet cap;

c. said expandable exhaust tube portion permitting rotational and longitudinal movement of said hypo-tube relative to said evacuation tube when in a relaxed, unexpanded state and engaging said evacuation tube to seal said hypo-tube in engagement with said exhaust tube when in an expanded state; and, d. means for causing said expandable exhaust tube to expand and engage said evacuation tube.

30. The catheter of claim 29, wherein jet pressure expands said expandable exhaust tube.

31. The catheter of claim 29, wherein said means for causing said expandable exhaust tube to expand comprises an aperture at a distal end portion of said expandable exhaust tube for receiving fluid emitted from said jet cap.

32. The catheter of claim 31, wherein said jet cap contains a rearwardly facing orifice opposite said aperture for directing a flow of said high pressure fluid into said expandable exhaust tube.

33. The catheter of claim 31, wherein said aperture includes a ramped annular surface.

34. The catheter of claim 29, further including flexible guidewire means affixed to, and extending outwardly from, in axial alignment with the distal end of said jet cap.

35. The catheter of claim 34, wherein said guidewire means comprises a coil spring and a tapered core.

36. The catheter of claim 35, wherein said tapered core is of a thickness of about 0.010 inches to 0.004 inches on proximal end to 0.004 inches to 0.002 inches on distal end.

37. The catheter of claim 29, wherein said solution in said longitudinally positionable high pressure hypo-tube is supplied at an infusion pressure in a range of 500 to 15,000 psi.

38. A method of removing material from a body cavity, the method comprising the steps of:

a. providing an outer assembly including a proximally located manifold, a distally extending evacuation catheter, and means to manipulate the evacuation catheter;

b. providing an inner assembly including a hypo-tube catheter, the hypo-tube catheter being movable within the outer assembly, means to manipulate the hypo-tube proximally coupled to the hypo-tube, and the hypo-tube having a distally located jet cap means to form a proximally directed jet from a high pressure flow of liquid in the hypo-tube, and a flow director, adjacent to but proximally spaced apart from the jet cap to receive at least a portion of the proximally directed jet, wherein the flow director includes a longitudinally oriented exhaust tube, movable within the evacuation catheter in the absence of a jet from the jet cap;

c. providing a guidewire;

d. advancing the guidewire percutaneously through vasculature to the material to be removed from the body cavity;

e. advancing the outer assembly over the guidewire to place the distal end of the outer assembly adjacent the material;

f. withdrawing the guidewire from within the outer assembly;

g. advancing the inner assembly within the outer assembly to extend the jet cap past the distal end of the outer assembly at a predetermined distance;

h. providing a high pressure liquid flow to the inner assembly to form a jet directed toward the expandable exhaust tube of the flow director of the inner assembly; and, i. allowing the formed jet to expand the expandable exhaust tube to seal against the outer assembly and entrain material to be removed into a proximally directed flow through the expandable exhaust tube and thence further proximally through the outer assembly and further to allow the impingement of the jet on the evacuation lumen to create sufficient stagnation pressure to allow evacuation of debris with no need for additional suction on the proximal end of the evacuation lumen.

39. A method of removing material from a body cavity, the method comprising the steps of:

a. providing an outer assembly including a proximally located manifold, a distally extending evacuation catheter, and means to manipulate the evacuation catheter interposed between the manifold and the evacuation catheter;

b. providing an inner assembly including a hypo-tube catheter, the hypo-tube catheter of the inner assembly being movable within the evacuation catheter, the manifold and the means to manipulate the evacuation catheter of the outer assembly, means to manipulate the hypo-tube proximally coupled to the hypo-tube, the means to manipulate the hypo-tube and means to limit maximum distal movement of the inner assembly relative to the outer assembly, both situated proximal to the manifold of the outer assembly, and the hypo-tube having a distally located jet cap means to form a proximally directed jet from a high pressure flow of liquid in the hypo-tube, and a flow director, adjacent to but proximally spaced apart a desired distance from the jet cap to receive a portion of the proximally directed jet, wherein the flow director includes a longitudinally oriented expandable exhaust tube, movable within the evacuation catheter in the absence of a jet from the jet cap and temporarily expandedly sealed within the evacuation catheter in response to the presence of a jet from the jet cap;

c. providing a guidewire;

d. advancing the guidewire percutaneously through vasculature to the material to be removed from the body cavity;

e. advancing the outer assembly over the guidewire to place the distal end of the outer assembly adjacent the material;

f. withdrawing the guidewire from within the outer assembly;

g. advancing the inner assembly within the outer assembly to extend the jet cap past the distal end of the outer assembly at a predetermined distance;

h. providing a high pressure liquid flow to the inner assembly to form a jet directed toward the expandable exhaust tube of the flow director of the inner assembly; and, i. allowing the formed jet to expand the expandable exhaust tube to seal against the outer assembly and entrain material to be removed into a proximally directed flow through the expandable exhaust tube and thence further proximally through the outer assembly.

* * * * *